United States Patent
McKearn et al.

(10) Patent No.: US 6,649,645 B1
(45) Date of Patent: Nov. 18, 2003

(54) COMBINATION THERAPY OF RADIATION AND A COX-2 INHIBITOR FOR TREATMENT OF NEOPLASIA

(75) Inventors: John P McKearn, St. Louis, MO (US); Jaime L Masferrer, Ballwin, MO (US); Luka Milas, Houston, TX (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/385,214

(22) Filed: Aug. 27, 1999

Related U.S. Application Data
(60) Provisional application No. 60/113,786, filed on Dec. 23, 1998.

(51) Int. Cl.[7] .............................. A61K 31/415
(52) U.S. Cl. ...................... 514/406; 514/403
(58) Field of Search ................. 514/403, 406

(56) References Cited

U.S. PATENT DOCUMENTS

| | | | |
|---|---|---|---|
| 3,840,597 A | 10/1974 | Moore et al. ............... | 260/556 |
| 4,233,299 A | 11/1980 | Trummlitz et al. .......... | 424/246 |
| 4,472,382 A | 9/1984 | Labrie et al. ................ | 424/177 |
| 4,596,797 A | 6/1986 | Schweikert et al. ......... | 514/177 |
| 4,659,695 A | 4/1987 | Labrie ......................... | 514/15 |
| 4,760,053 A | 7/1988 | Labrie ......................... | 514/15 |
| 4,775,660 A | 10/1988 | Labrie et al. ................ | 514/15 |
| 5,380,738 A | 1/1995 | Norman et al. .............. | 514/374 |
| 5,393,790 A | 2/1995 | Reitz et al. .................. | 514/709 |
| 5,409,944 A | 4/1995 | Black et al. ................. | 514/359 |
| 5,418,254 A | 5/1995 | Huang et al. ................ | 514/604 |
| 5,420,343 A | 5/1995 | Koszyk et al. .............. | 562/468 |
| 5,434,178 A | 7/1995 | Talley et al. ................ | 514/406 |
| 5,466,823 A | 11/1995 | Talley et al. ............. | 548/377.1 |
| 5,474,995 A | 12/1995 | Ducharme et al. .......... | 514/241 |
| 5,486,534 A | 1/1996 | Lee et al. .................... | 514/406 |
| 5,504,215 A | 4/1996 | Talley et al. ............. | 548/377.1 |
| 5,508,426 A | 4/1996 | Talley et al. ............. | 548/359.1 |
| 5,510,368 A | 4/1996 | Lau et al. .................... | 514/419 |
| 5,510,496 A | 4/1996 | Talley et al. ............. | 548/365.7 |

(List continued on next page.)

FOREIGN PATENT DOCUMENTS

| | | |
|---|---|---|
| EP | 595546 | 3/1996 |
| EP | 799823 | 10/1997 |
| EP | 927555 | 7/1999 |
| EP | 985666 | 3/2000 |
| WO | 93/18652 | 9/1993 |
| WO | 94/13635 | 6/1994 |
| WO | 94/14977 | 7/1994 |
| WO | 94/159321 | 7/1994 |
| WO | 94/20480 | 9/1994 |
| WO | 94/26731 | 11/1994 |
| WO | 94/27980 | 12/1994 |
| WO | 95/00501 | 1/1995 |
| WO | 95/09238 | 4/1995 |
| WO | 95/11883 | 5/1995 |
| WO | 95/15316 | 6/1995 |

(List continued on next page.)

OTHER PUBLICATIONS

Taketo, Makoto M. "Cyclooxygenase–2 inhibitors in tumorigenesis (part 1)", J. Natl. Cancer Inst. 1998, 90(20), 1529–1536, CODEN: JNCIEQ; ISSN: 0027–8874.*

Phelps, H. M. "Curative radiation therapy for early breast cancer.", Journal of the Maine Medical Association, (1978) 69/9 (248–250) CODEN: JMMAA7.*

(List continued on next page.)

Primary Examiner—Theodore J. Criares
Assistant Examiner—Jennifer Kim
(74) Attorney, Agent, or Firm—Joseph W. Bulock; James M. Warner

(57) ABSTRACT

The present invention provides methods to treat or prevent neoplasia disorders in a mammal using a combination of radiation therapy and a cyclooxygenase-2 inhibitor.

23 Claims, 4 Drawing Sheets

U.S. PATENT DOCUMENTS

| | | | |
|---|---|---|---|
| 5,516,907 A | 5/1996 | Talley et al. | 548/365.7 |
| 5,521,207 A | 5/1996 | Graneto | 514/406 |
| 5,521,213 A | 5/1996 | Prasti et al. | 514/443 |
| 5,536,752 A | 7/1996 | Ducharme et al. | 514/602 |
| 5,543,933 A | 8/1996 | Kang et al. | 358/335 |
| 5,547,975 A | 8/1996 | Talley et al. | 514/406 |
| 5,550,142 A | 8/1996 | Ducharme et al. | 514/365 |
| 5,552,422 A | 9/1996 | Gauthler et al. | 514/368 |
| 5,563,165 A | 10/1996 | Talley et al. | 514/406 |
| 5,565,482 A | 10/1996 | Talley et al. | 514/406 |
| 5,576,339 A | 11/1996 | Huang et al. | 514/345 |
| 5,580,985 A | 12/1996 | Lee et al. | 548/364.1 |
| 5,596,008 A | 1/1997 | Lee | 514/347 |
| 5,604,253 A | 2/1997 | Lau et al. | 514/415 |
| 5,604,260 A | 2/1997 | Guay et al. | 514/605 |
| 5,616,458 A | 4/1997 | Lipsky et al. | 435/4 |
| 5,616,601 A | 4/1997 | Khanna et al. | 514/399 |
| 5,620,999 A | 4/1997 | Weier et al. | 514/398 |
| 5,633,272 A | 5/1997 | Talley et al. | 514/378 |
| 5,639,780 A | 6/1997 | Lau et al. | 514/419 |
| 5,663,180 A | 9/1997 | Reitz et al. | 514/299 |
| 5,663,195 A | 9/1997 | Scolnick et al. | 514/461 |
| 5,668,161 A | 9/1997 | Talley et al. | 514/365 |
| 5,670,510 A | 9/1997 | Huang et al. | 514/278 |
| 5,670,532 A | 9/1997 | Talley et al. | 514/403 |
| 5,672,626 A | 9/1997 | Huang et al. | 514/520 |
| 5,672,627 A | 9/1997 | Huang et al. | 514/520 |
| 5,677,318 A | 10/1997 | Lau | 514/361 |
| 5,681,842 A | 10/1997 | Dellaria et al. | 514/367 |
| 5,686,460 A | 11/1997 | Nicolia et al. | 514/277 |
| 5,686,470 A | 11/1997 | Weier et al. | 514/334 |
| 5,691,374 A | 11/1997 | Black et al. | 514/473 |
| 5,696,143 A | 12/1997 | Talley et al. | 514/403 |
| 5,698,584 A | 12/1997 | Black et al. | 514/462 |
| 5,719,163 A | 2/1998 | Norman et al. | 514/311 |
| 5,733,909 A | 3/1998 | Black et al. | 514/238.8 |
| 5,736,579 A | 4/1998 | Reitz et al. | 514/709 |
| 5,739,166 A | 4/1998 | Reitz et al. | 514/602 |
| 5,753,688 A | 5/1998 | Talley et al. | 514/406 |
| 5,756,530 A | 5/1998 | Lee et al. | 514/406 |
| 5,760,060 A | 6/1998 | Talley et al. | 514/403 |
| 5,776,967 A | 7/1998 | Kreft et al. | 514/411 |
| 5,783,597 A | 7/1998 | Beers et al. | 5147/447 |
| 5,789,413 A | 8/1998 | Black et al. | 514/255 |
| 5,811,425 A | 9/1998 | Woods et al. | 514/249 |
| 5,830,911 A | 11/1998 | Failli et al. | 514/411 |
| 5,840,924 A | 11/1998 | Desmond et al. | 549/323 |
| 5,849,943 A | 12/1998 | Atkinson et al. | 560/8 |
| 5,859,036 A | 1/1999 | Sartori et al. | 514/369 |
| 5,859,257 A | 1/1999 | Talley | 548/247 |
| 5,863,946 A | 1/1999 | Brooks et al. | 514/564 |
| 5,869,524 A | 2/1999 | Failli | 514/473 |
| 5,883,267 A | 3/1999 | Rossen et al. | 549/319 |
| 5,908,852 A | 6/1999 | Talley et al. | 514/340 |
| 5,908,858 A | 6/1999 | Talley | 548/247 |
| 5,916,905 A | 6/1999 | Weier et al. | 514/345 |
| 5,919,809 A | 7/1999 | Ehrgott et al. | 514/418 |
| 5,922,742 A | 7/1999 | Black et al. | 514/345 |
| 5,932,598 A | 8/1999 | Talley et al. | 514/341 |
| 5,932,994 A | 8/1999 | Ju et al. | 323/222 |
| 5,935,990 A | 8/1999 | Khanna et al. | 514/423 |
| 5,972,986 A | 10/1999 | Seibert et al. | 516/406 |
| 6,028,072 A | 2/2000 | Lee et al. | 514/256 |
| 6,034,256 A | 3/2000 | Carter et al. | 549/456 |
| 6,274,590 B1 | 8/2001 | Talley et al. | 514/277 |
| 6,432,999 B2 | 8/2002 | Talley et al. | 514/406 |
| 6,436,967 B1 | 8/2002 | Talley et al. | 514/341 |

FOREIGN PATENT DOCUMENTS

| | | |
|---|---|---|
| WO | 95/15318 | 6/1995 |
| WO | 95/18799 | 7/1995 |
| WO | 95/21817 | 8/1995 |
| WO | 95/30652 | 11/1995 |
| WO | 95/30656 | 11/1995 |
| WO | 96/38418 | 11/1995 |
| WO | 96/03385 | 2/1996 |
| WO | 96/03387 | 2/1996 |
| WO | 96/03388 | 2/1996 |
| WO | 96/03392 | 2/1996 |
| WO | 96/06840 | 3/1996 |
| WO | 96/08482 | 3/1996 |
| WO | 96/09293 | 3/1996 |
| WO | 96/09304 | 3/1996 |
| WO | 96/11676 | 4/1996 |
| WO | 96/12483 | 5/1996 |
| WO | 96/13483 | 5/1996 |
| WO | 96/16934 | 6/1996 |
| WO | 96/19462 | 6/1996 |
| WO | 96/19463 | 6/1996 |
| WO | 96/19469 | 6/1996 |
| WO | 96/21667 | 7/1996 |
| WO | 96/23786 | 8/1996 |
| WO | 96/24584 | 8/1996 |
| WO | 96/24585 | 8/1996 |
| WO | 96/24604 | 8/1996 |
| WO | 96/25405 | 8/1996 |
| WO | 96/25928 | 8/1996 |
| WO | 96/26921 | 9/1996 |
| WO | 96/31509 | 10/1996 |
| WO | 96/36617 | 11/1996 |
| WO | 96/36623 | 11/1996 |
| WO | 96/37467 | 11/1996 |
| WO | 96/37468 | 11/1996 |
| WO | 96/37469 | 11/1996 |
| WO | 96/38418 | 12/1996 |
| WO | 96/38442 | 12/1996 |
| WO | 96/39144 | 12/1996 |
| WO | 96/40143 | 12/1996 |
| WO | 96/41625 | 12/1996 |
| WO | 96/41626 | 12/1996 |
| WO | 96/41645 | 12/1996 |
| WO | 97/03667 | 2/1997 |
| WO | 97/03953 | 2/1997 |
| WO | 97/09977 | 3/1997 |
| WO | 97/10840 | 3/1997 |
| WO | 97/11701 | 4/1997 |
| WO | 97/11704 | 4/1997 |
| WO | 97/13755 | 4/1997 |
| WO | 97/13767 | 4/1997 |
| WO | 97/14679 | 4/1997 |
| WO | 97/14691 | 4/1997 |
| WO | 97/16435 | 5/1997 |
| WO | 97/25045 | 7/1997 |
| WO | 97/25046 | 7/1997 |
| WO | 97/25047 | 7/1997 |
| WO | 97/25048 | 7/1997 |
| WO | 97/27181 | 7/1997 |
| WO | 97/28120 | 8/1997 |
| WO | 97/28121 | 8/1997 |
| WO | 97/29774 | 8/1997 |
| WO | 97/29775 | 8/1997 |
| WO | 97/29776 | 8/1997 |
| WO | 97/30030 | 8/1997 |
| WO | 97/31631 | 9/1997 |
| WO | 97/34882 | 9/1997 |
| WO | 97/36497 | 10/1997 |
| WO | 97/36863 | 10/1997 |
| WO | 97/37984 | 10/1997 |
| WO | 97/38686 | 10/1997 |

| | | |
|---|---|---|
| WO | 97/40012 | 10/1997 |
| WO | 97/44027 | 11/1997 |
| WO | 97/44028 | 11/1997 |
| WO | 97/45420 | 12/1997 |
| WO | 97/46524 | 12/1997 |
| WO | 97/46532 | 12/1997 |
| WO | 98/00416 | 1/1998 |
| WO | 98/03484 | 1/1998 |
| WO | 98/04527 | 2/1998 |
| WO | 98/05639 | 2/1998 |
| WO | 98/05643 | 2/1998 |
| WO | 98/06708 | 2/1998 |
| WO | 98/06715 | 2/1998 |
| WO | 98/07425 | 2/1998 |
| WO | 98/07714 | 2/1998 |
| WO | 98/11080 | 3/1998 |
| WO | 98/15528 | 4/1998 |
| WO | 98/16227 | 4/1998 |
| WO | WO-9816227 A1 * | 4/1998 |
| WO | 98/17292 | 4/1998 |
| WO | 98/21195 | 5/1998 |
| WO | 98/22101 | 5/1998 |
| WO | 98/22104 | 5/1998 |
| WO | 98/22442 | 5/1998 |
| WO | 98/22457 | 5/1998 |
| WO | 98/24782 | 6/1998 |
| WO | 98/25896 | 6/1998 |
| WO | 98/39330 | 9/1998 |
| WO | 98/41511 | 9/1998 |
| WO | 98/41516 | 9/1998 |
| WO | 98/43966 | 10/1998 |
| WO | 98/46594 | 10/1998 |
| WO | 98/47871 | 10/1998 |
| WO | 98/47890 | 10/1998 |
| WO | 98/57924 | 12/1998 |
| WO | 99/05104 | 2/1999 |
| WO | 99/10331 | 3/1999 |
| WO | 99/10332 | 3/1999 |
| WO | 99/11605 | 3/1999 |
| WO | 99/12930 | 3/1999 |
| WO | 99/14194 | 3/1999 |
| WO | 99/14195 | 3/1999 |
| WO | 99/15503 | 4/1999 |
| WO | 99/15505 | 4/1999 |
| WO | 99/18960 | 4/1999 |
| WO | 99/23087 | 5/1999 |
| WO | 99/24025 | 5/1999 |
| WO | 99/33796 | 7/1999 |
| WO | 99/35130 | 7/1999 |

OTHER PUBLICATIONS

Moskowitz & Coughlins, Stroke, 1981, 12,882–86.
Leung & Mihich, Nature, 1980, 597–600.
Honn et al., Prostaglandins, 1981, 21, 833–64.
Isakson et al., Adv. Pros. Throm. Leuk. Res., 1995, 23, 49–54.
Milas et al., Cancer Res., 1990, 50, 4473–7.
Weppelmann & Monkemeier, Gyn. Onc., 1984, 47, 196–9.
Kumar & Armstrong, Emerging Drugs, 1997, 2, 175–190.
Gorski et al., Cancer Res., 1998, 5686–9.
Masferrer et al., Proc. Am. Assoc. Cancer Research, 1999, 40, 396.
Masferrer et al., $89^{th}$ Annual Meeting of the American Association for Cancer Research, Mar. 1998.
J. Clin. Oncol., 10, 1992, 829–838.
Pharmacology, 41, 1990, 177–183.
Tetragenesis, Carcinogenesis, & Mutagenesis, 10, 1990, 477–501.
Haskel, Chest., 99, 1991, 1325.
Bakowsk, Cancer Treat. Rev., 10, 1983, 159.
Joss, Cancer Treat Rev., 11, 1984, 205.
Ihde, Cancer, 54, 1984, 2722.
Cancer Surveys, Breast Cancer, 19, Cold Spring Harbor Laboratory Press, 1993.
Heron, J. Statist. Comut. Simul., 3, 1975, 265–74.

* cited by examiner

COMBINATION THERAPY OF RADIATION AND A COX-2 INHIBITOR FOR TREATMENT OF NEOPLASIA

RELATED CASE

This application is a Provisional Application claimed benefit of U.S. patent application Ser. No. 60/113,786, filed Dec. 23, 1998.

FIELD OF THE INVENTION

The present invention relates to a combination of radiation therapy and a cyclooxygenase-2 (COX-2) inhibitor for treatment of neoplasia disorders. More specifically, this invention relates to the use of COX-2 inhibitors in combination with radiation therapy for treating cancer.

BACKGROUND OF THE INVENTION

A neoplasm, or tumor, is an abnormal, unregulated, and disorganized proliferation of cell growth. A neoplasm is malignant, or cancerous, if it has properties of destructive growth, invasiveness and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphotics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Cancer is now the second leading cause of death in the United States and over 8,000,000 persons in the United States have been diagnosed with cancer. In 1995, cancer accounted for 23.3% of all deaths in the United States.

Cancer is not fully understood on the molecular level. It is known that exposure of a cell to a carcinogen such as certain viruses, certain chemicals, or radiation, leads to DNA alteration that inactivates a "suppressive" gene or activates an "oncogene". Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality.

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, inaccessible to surgeons, nor in the treatment of disseminated neoplastic conditions such as leukemia.

Chemotherapy involves the disruption of cell replication or cell metabolism. It is used most often in the treatment of breast, lung, and testicular cancer.

The adverse effects of systemic chemotherapy used in the treatment of neoplastic disease is most feared by patients undergoing treatment for cancer. Of these adverse effects nausea and vomiting are the most common and severe side effects. Other adverse side effects include cytopenia, infection, cachexia, mucositis in patients receiving high doses of chemotherapy with bone marrow rescue or radiation therapy; alopecia (hair loss); cutaneous complications such as pruritis, urticaria, and angioedema; neurological complications; pulmonary and cardiac complications in patients receiving radiation or chemotherapy; and reproductive and endocrine complications (M. Abeloff, et al., Alopecia and Cutaneous Complications, in Clinical Oncology 755–56 (Abeloff, ed. 1992).

Chemotherapy-induced side effects significantly impact the quality of life of the patient and may dramatically influence patient compliance with treatment.

Additionally, adverse side effects associated with chemotherapeutic agents are generally the major dose-limiting toxicity (DLT) in the administration of these drugs. For example, mucositis, is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe, may lead to hospitalization, or require treatment with analgesics for the treatment of pain.

In general, radiation therapy is employed as potentially curative therapy for patients who present with clinically localized disease and are expected to live at least 10 years.

For example, approximately 70% of newly diagnosed prostate cancer patients fall into this category. Approximately 10% of these patients (7% of total patients) undergo radiation therapy. Approximately 80% of patients who have undergone radiation as their primary therapy have disease persistence or develop recurrence or metastasis within five years after treatment. Currently, most of these radiotherapy patients generally do not receive any immediate follow-up therapy. Rather, they are monitored frequently, such as for elevated Prostate Specific Antigen ("PSA"), which is the primary indicator of recurrence or metastasis in prostate cancer.

The adverse side effects induced by chemotherapeutic agents and radiation therapy have become of major importance to the clinical management of cancer patients.

Colorectal Cancer

Survival from colorectal cancer depends on the stage and grade of the tumor, for example precursor adenomas to metastatic adenocarcinoma. Generally, colorectal cancer can be treated by surgically removing the tumor, but overall survival rates remain between 45 and 60 percent. Colonic excision morbidity rates are fairly low and is generally associated with the anastomosis and not the extent of the removal of the tumor and local tissue. In patients with a high risk of reoccurrence, however, chemotherapy has been incorporated into the treatment regimen in order to improve survival rates.

Tumor metastasis prior to surgery is generally believed to be the cause of surgical intervention failure and up to one year of chemotherapy is required to kill the non-excised tumor cells. As severe toxicity is associated with the chemotherapeutic agents, only patients at high risk of recurrence are placed on chemotherapy following surgery.

Prostate Cancer

Prostate cancer is now the leading form of cancer among men and the second most frequent cause of death from cancer in men. It is estimated that more than 165,000 new cases of prostate cancer were diagnosed in 1993, and more than 35,000 men died from prostate cancer in that year. Additionally, the incidence of prostate cancer has increased by 50% since 1981, and mortality from this disease has continued to increase. Previously, most men died of other illnesses or diseases before dying from their prostate cancer. We now face increasing morbidity from prostate cancer as men live longer and the disease has the opportunity to progress.

Current therapies for prostate cancer focus upon reducing levels of dihydrotestosterone to decrease or prevent growth of prostate cancer. Radiation alone or in combination with surgery and/or chemotherapeutic agents is often used.

In addition to the use of digital rectal examination and transrectal ultrasonography, prostate-specific antigen (PSA) concentration is frequently used in the diagnosis of prostate cancer.

U.S. Pat. No. 4,472,382 discloses treatment of benign prostatic hyperplasia (BPH) with an antiandrogen and certain peptides which act as LH-RH agonists. U.S. Pat. No. 4,596,797 discloses aromatase inhibitors as a method of prophylaxis and/or treatment of prostatic hyperplasia. U.S. Pat. No. 4,760,053 describes a treatment of certain cancers which combines an LHRH agonist with an antiandrogen and/or an antiestrogen and/or at least one inhibitor of sex steroid biosynthesis. U.S. Pat. No. 4,775,660 discloses a method of treating breast cancer with a combination therapy which may include surgical or chemical prevention of ovarian secretions and administering an antiandrogen and an antiestrogen. U.S. Pat. No. 4,659,695 discloses a method of treatment of prostate cancer in susceptible male animals including humans whose testicular hormonal secretions are blocked by surgical or chemical means, e.g. by use of an LHRH agonist, which comprises administering an antiandrogen, e.g. flutamide, in association with at least one inhibitor of sex steroid biosynthesis, e.g. aminoglutethimide and/or ketoconazole.

Prostate Specific Antigen

One well known prostate cancer marker is Prostate Specific Antigen (PSA). PSA is a protein produced by prostate cells and is frequently present at elevated levels in the blood of men who have prostate cancer. PSA has been shown to correlate with tumor burden, serve as an indicator of metastatic involvement, and provide a parameter for following the response to surgery, irradiation, and androgen replacement therapy in prostate cancer patients. It should be noted that Prostate Specific Antigen (PSA) is a completely different protein from Prostate Specific Membrane Antigen (PSMA). The two proteins have different structures and functions and should not be confused because of their similar nomenclature.

Prostate Specific Membrane Antigen (PSMA)

In 1993, the molecular cloning of a prostate-specific membrane antigen (PSMA) was reported as a potential prostate carcinoma marker and hypothesized to serve as a target for imaging and cytotoxic treatment modalities for prostate cancer. Antibodies against PSMA have been described and examined clinically for diagnosis and treatment of prostate cancer. In particular, Indium-111 labelled PSMA antibodies have been described and examined for diagnosis of prostate cancer and itrium-labelled PSMA antibodies have been described and examined for the treatment of prostate cancer.

Pancreas Cancer

Approximately 2% of new cancer cases diagnoses in the United States is pancreatic cancer. Pancreatic cancer is generally classified into two clinical types: 1) adenocarcinoma (metastatic and non-metastatic), and 2) cystic neoplasms (serous cystadenomas, mucinous cystic neoplasms, papilary cystic neoplasms, acinar cell systadenocarcinoma, cystic choriocarcinoma, cystic teratomas, angiomatous neoplasms).

Ovary Cancer

Celomic epithelial carcinoma accounts for approximately 90% of ovarian cancer cases. Preferred single agents that can be used in combination include: alkylating agents, ifosfamide, cisplatin, carboplatin, taxol, doxorubicin, 5-fluorouracil, methotrexate, mitomycin, hexamethylmelamine, progestins, antiestrogens, prednimustine, dihydroxybusulfan, galactitol, interferon alpha and interferon gamma.

Cancer of the fallopian tube is the least common type of ovarian cancer, accounting for approximately 400 new cancer cases per year in the United States. Papillary serous adenocarcinoma accounts for approximately 90% of all malignancies of the ovarian tube.

Prostaglandins are arachidonate metabolites produced in virtually all mammalian tissues and possess diverse biologic capabilities, including vasoconstriction, vasodilation, stimulation or inhibition of platelet aggregation, and immunomodulation, primarily immunosupression (Moskowitz and Coughlins, *Stroke* 1981; 12: 882–86; Leung and Mihich. *Nature* 1980; 597–600; Brunda et al., *J. Immunol.* 1980; 124: 2682–7). They are implicated in the promotion of development and growth of malignant tumors (Honn et al., *Prostaglandins* 1981;21:833–64; Furuta et al., *Cancer Res.* 1989, 48, 3002–7; Taketo; *J. Natl. Cancer Inst.* 1998, 90, 1609–20). They are also involved in the response of tumor and normal tissues to cytotoxic agents such as ionizing radiation (Milas and Hanson, *Eur. J. Cancer* 1995, 31A, 1580–5). Prostaglandin production is mediated by two cyclooxygenase enzymes: COX-1 and COX-2. Cyclooxygenase-1 (COX-1) is constitutively expressed and is ubiquitous. Cyclooxygenase-2 (COX-2) is induced by diverse inflammatory stimuli (Isakson et al., *Adv. Pros. Throm. Leuk Res.* 1995, 23, 49–54).

Prostaglandin-mediated effects at both the microenvironmental and cellular levels have been implicated in the modulation of such response. Prostaglandin $E_2$, and prostaglandin $I_2$ protect jejunum crypt cells, and prostaglandin $I_2$ protects B16 melanoma cells from radiation damage. Inhibition of prostaglandin synthesis also induces an accumulation of cells in the $G_2+M$ phases of the cell cycle, which are generally considered to be the most sensitive to ionizing radiation. With the inhibition of prostaglandin synthesis, prostaglandin-induced immunosuppressive activity was diminished and antitumor immunologic responses were able to potentiate tumor response to radiation. Finally, prostaglandins are vasoactive agents and are thus likely to regulate tumor blood flow and perfusion.

Nonsteroidal anti-inflammatory drugs (NSAIDs) non-selectively inhibit both cyclooxygenase enzymes and consequently can prevent, inhibit, or abolish the effects of prostaglandins. Increasing evidence shows that NSAIDs can inhibit the development of cancer in both experimental animals and in humans, can reduce the size of established tumors, and can increase the efficacy of cytotoxic cancer chemotherapeutic agents. Our own investigations have demonstrated that indomethacin prolongs tumor growth delay and increases the tumor cure rate in mice after radiotherapy (Milas et al., *Cancer Res.* 1990, 50, 4473–7). The influence of oxyphenylbutazone and radiation therapy on cervical cancer has been studied. (Weppelmann and Monkemeier, *Gyn. Onc.*, 1984, 47, 196–9).

However, treatment with NSAIDs are limited by toxicity to normal tissue, particularly by ulcerations and bleeding in the gastrointestinal tract, ascribed to the inhibition of COX-1. Recently developed selective COX-2 inhibitors exert potent anti-inflammatory activity but cause fewer side effects.

Antiangiogenesis therapy has been used as an adjunct to chemotherapy, radiation therapy, or surgery. (Kumar and Armstrong, *Emerging Drugs* 1997, 2, 175–190). Recently, it was reported that the combination of radiation with antiangiogenic compounds produces an additive effect on the growth of human tumor xenografts (Gorski et al., *Cancer Res.* 1998; 58, 5686–9).

COX-2 inhibitors have been described for the treatment of cancer (WO98/16227) and for the treatment of tumors (EP 927,555). Celecoxib, a specific inhibitor of COX-2, exerted a potent inhibition of fibroblast growth factor-induced corneal angiogenesis in rats. (Masferrer et al., *Proc. Am. Assoc. Cancer Research* 1999, 40, 396). COX-2 specific inhibitors prevent angiogenesis in experimental animals, but their efficacy in enhancing in vivo tumor response to radiation has not been established.

DETAILED DESCRIPTION OF THE INVENTION

Figure 1:
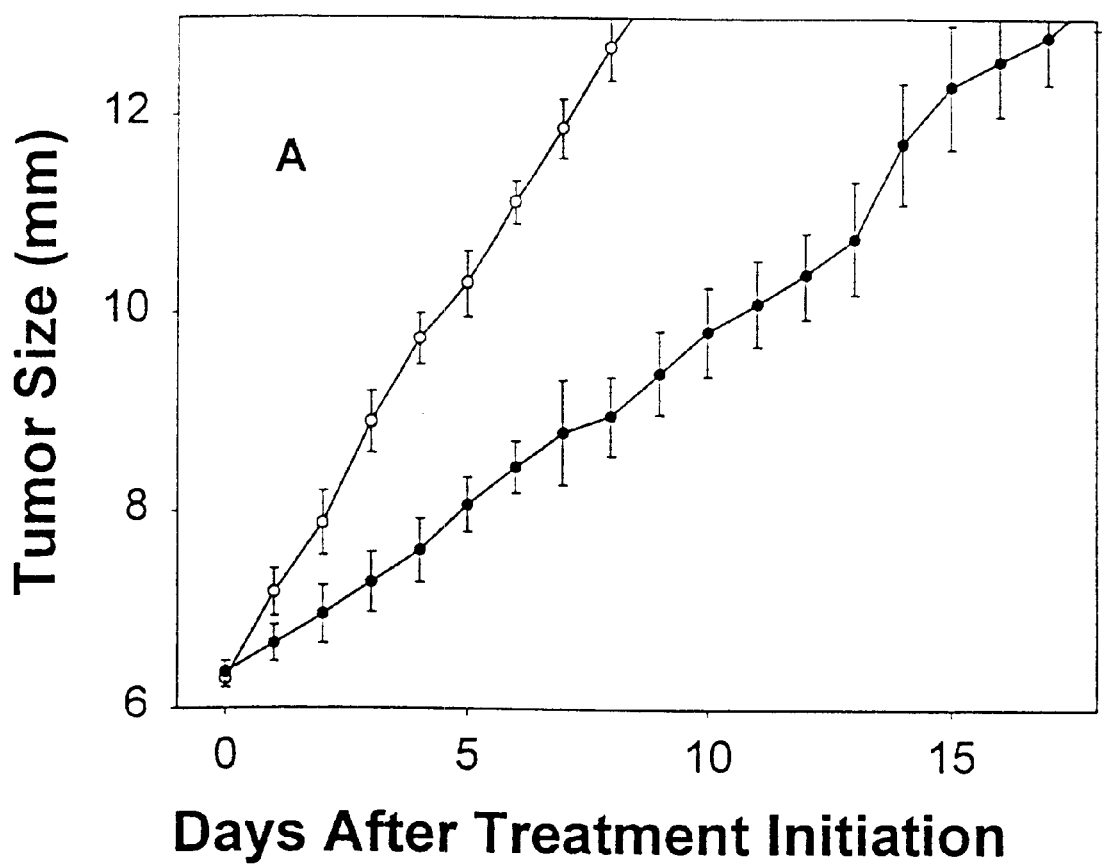
FIG. 1 shows the effect of a COX-2 inhibitor (4-[5-(4-chlorophenyl)-3-trifluoromethyl-1H-pyrazol-1-yl] benzenesulfonamide) on tumor growth.

Treatment of a neoplasia disorder in a mammal in need of such treatment is provided by methods and combinations using radiation and a COX-2 inhibitor. The method comprises treating a mammal with a therapeutically effective amount of a combination comprising a COX-2 inhibitor and a radiotherapeutic agent.

Specific inhibitors of COX-2 potentiate tumor response to radiation. Thus, COX-2 inhibitors improve the efficacy of radiotherapy.

In one embodiment of the invention a method for treating neoplasia in a subject in need of such treatment comprises treating the subject with radiation therapy and a therapeutically effective amount of a cyclooxygenase-2 inhibitor or pharmaceutically acceptable salt or derivative thereof wherein the neoplasia is selected from lung cancer, breast cancer, gastrointestinal cancer, bladder cancer, head and neck cancer, and cervical cancer.

The methods and combinations of the present invention may be used for the treatment of neoplasia disorders selected from the group consisting of acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondrosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiatied carcinoma, uveal melanoma, verrucous carcinoma, vipoma, well differentiated carcinoma, and Wilm's tumor.

The methods and compositions of the present invention provide one or more benefits. A combination of a COX-2 inhibitor with radiation therapy of the present invention are useful in treating neoplasia disorders. Preferably, the COX-2 inhibitor agent or agents and the radiation therapies of the present invention are administered in combination at a low dose, that is, at a dose lower than has been conventionally used in clinical situations for each of the individual components administered alone.

A benefit of lowering the dose of the radiation therapies of the present invention administered to a mammal includes a decrease in the incidence of adverse effects associated with higher dosages.

By lowering the incidence of adverse effects, an improvement in the quality of life of a patient undergoing treatment for cancer is contemplated. Further benefits of lowering the incidence of adverse effects include an improvement in patient compliance, and a reduction in the number of hospitalizations needed for the treatment of adverse effects.

Alternatively, the methods and combination of the present invention can also maximize the therapeutic effect at higher doses.

The term "pharmaceutically acceptable" is used herein to mean that the modified noun is appropriate for use in a pharmaceutical product. Pharmaceutically acceptable cations include metallic ions and organic ions. More preferred metallic ions include, but are not limited to appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

Also included in the combination of the invention are the isomeric forms and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically-acceptable base addition salts of compounds of the present invention include metallic ion salts and organic ion salts. More preferred metallic ion salts include, but are not limited to appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

A COX-2 inhibitor of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences,* Mack Publishing Co., Easton, Pa.; 1975 and Liberman, H. A. and Lachman, L., Eds., *Pharmaceutical Dosage Forms,* Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and nonionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated COX-2 inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

The term "treatment" refers to any process, action, application, therapy, or the like, wherein a mammal, including a human being, is subject to medical aid with the object of improving the mammal's condition, directly or indirectly.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention.

The term "prevention," in relation to neoplasia, tumor growth or tumor cell growth, means no tumor or tumor cell growth if none had occurred, no further tumor or tumor cell growth if there had already been growth.

Angiogenesis is an attractive therapeutic target because it is a multi-step process that occurs in a specific sequence, thus providing several possible targets for drug action. Examples of agents that interfere with several of these steps include specific COX-2 inhibitors, that prevent the growth of cells that form new blood vessels.

The phrase "therapeutically-effective" is intended to qualify the amount of each agent that will achieve the goal of improvement in neoplastic disease severity and the frequency of incidence over treatment of each agent by itself, while avoiding adverse side effects typically associated with alternative therapies.

A "therapeutic effect" relieves to some extent one or more of the symptoms of a neoplasia disorder. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

"Therapeutic effective amount" is intended to qualify the amount required to achieve a therapeutic effect.

The phrases "low dose" or "low dose amount", in characterizing a therapeutically effective amount of the COX-2 inhibitor and the radiation or therapy in the combination therapy, defines a quantity of such therapy, or a range of quantity of such therapy, that is capable of diminishing the neoplastic disease while reducing or avoiding one or more radiation-induced side effects, such as myelosupression, cardiac toxicity, skin erythema and desquamation, alopecia, inflammation or fibrosis.

The phrase "adjunctive therapy" includes agents such as those, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The phrase a "radiotherapeutic agent" refers to the use of electromagnetic or particulate radiation in the treatment of neoplasia. Examples of radiotherapeutic agents are provided in, but not limited to, radiation therapy and is known in the art (Hellman, Principles of Radiation Therapy, Cancer, in Principles and Practice of Oncology, 248–75 (Devita et al., ed., 4th edit., volume 1, 1993).

The phrase "COX-2 inhibitor" includes agents that specifically inhibit a class of enzymes, the COX-2 enzyme. Preferably, it includes compounds which have a COX-2 $IC_{50}$ of less than about 1.0 $\mu M$, and more preferably of less than about 0.1 $\mu M$, and also have a selectivity ratio of COX-2 inhibition over COX-1 inhibition of at least 50, and more preferably of at least 100. Examples of COX-2 inhibitors are provided in, but not limited to, Table Nos. 1 and 2.

The referenced tables provided herein, provides non-exhaustive examples of each subtype that may be used in combinations and methods of the present invention

TABLE 1

COX-2 Inhibitors

| Compound | Trade Name | Company | Mode of Action | Reference | Dosage | Toxicity | Cancer Indication |
|---|---|---|---|---|---|---|---|
| lornoxicam | Safem | Roche Holding AG | Cyclooxygenase inhibitor | | | Cynomolgus monkeys: 1–2 mg/kg/day orally for six weeks | |
| 1,5-Diphenyl-3-substituted pyrazoles | | Fujisawa Pharmaceutical Co Ltd | Cyclooxygenase 2 inhibitor | WO-09713755 | | | |
| radicicol | | Scripps Research Institute | Tyrosine kinase inhibitor, Cyclooxygenase 2 modulator, IL-1 antagonist, TNF alpha antagonist | WO-09625928; Kwon et al (Cancer Res(1992) 52 6296) | | | |
| N-benzyl-3-indoleacetic acids | | Merck & Co Inc | Cyclooxygenase inhibitor, Anticancer | U.S. Pat. No. -05510368 | | | |
| GB-02283745 | | Merck & Co Inc | Cyclooxygenase 2 inhibitor | | | | |
| TP-72 | | Dartmouth Medical School | NO synthesis inhibitor, Cyclooxygenase 2 inhibitor | Cancer Res 1998 58 4 717 -723 | | | |
| Indene inhibitors of cox-2 | | American Home Products Corp | Cyclooxygenase 2 inhibito | WO-09821195 | | | |

TABLE 1-continued

COX-2 Inhibitors

| Compound | Trade Name | Company | Mode of Action | Reference | Dosage | Toxicity | Cancer Indication |
|---|---|---|---|---|---|---|---|
| carbocyclic diarylmethylene derivatives | | Bristol-Myers Squibb Co | Cyclooxygenase 2 inhibitor | WO-09805643 | | Rat: >300 mg/kg po | |
| 1,2-Diarylindole | | Bristol-Myers Squibb Co | Cyclooxygenase 2 inhibitor | WO-09805639 | | | |
| 1,2-Bisarylcyclobutene derivatives | | Merck & Co Inc | Cyclooxygenase 2 inhibitor | WO-09736863 | | | |
| Novel stilbene derivatives as prodrug forms of the diphenylcyclopentenones claimed in U.S. Pat. No. 05474995, WO-09500501 and WO-09518799. | | Merck & Co Inc | Cyclooxygenase 2 inhibitor | WO-09728121 | | | |
| 2,4-Diphenylbutenoic acid derivatives as prodrugs of COX-2 inhibitors claimed in U.S. Pat. No. 05474995, WO-09500501 and WO-09518799. | | Merck & Co Inc | | WO-09728120 | | | |
| 1-(4-chlorobenzoyl)-3-[4-(4-fluorophenyl)thiazol-2-ylmethyl]-5-methoxy-2-methy lindole | A-183827.0 | Abbott | Cyclooxygenase 2 inhibitor | | | | |
| | COX-2 inhibitor, Merck | Merck & Co | Cyclooxygenase 2 inhibitor | WO 9518799; WO 9608482; WO 9606840; WO 9621667; WO 9636623; WO 9744027 | | | Colon cancer |
| Sulfonamide substituted diarylthiazole | CS-179 | Monsanto | Cyclooxygenase 2 inhibitor | | | | |
| | GR-253035 | Glaxo Wellcome | Cyclooxygenase 2 inhibitor | | | | Chronic inflammatory pain Pain |
| 4-(4-cyclohexyl-2-methyloxazol-5-yl)-2-fluorobenzenesulfonamide | JTE-522 | Japan Tobacco | Cyclooxygenase 2 inhibitor | | | | |
| 5,6-diarylthiazolo[3,2-B][1,2,4]triazolo | L-768277 | Merck & Co | Cyclooxygenase 2 inhibitor | | | | |
| | L-783003 | Merck & Co | Cyclooxygenase 2 inhibitor | | | | |
| | MK-966 | Merck & Co | Cyclooxygenase 2 inhibitor | | 12.5–100 mg po | | |
| indometacin-derived indolalkanoic acid | | Merck & Co | Cyclooxygenase 2 inhibitor | WO 9637467-9 | 200 mg/kg/day | | |
| 1-Methylsulfonyl-4-[1,1-dimethyl-4-(4-fluorophenyl)cyclopenta-2,4-dien-3-yl]benzene | | Monsanto | Cyclooxygenase 2 inhibitor | WO 9530656; WO 9530652; WO 9638418; WO 9638442 | | | |

TABLE 1-continued

COX-2 Inhibitors

| Compound | Trade Name | Company | Mode of Action | Reference | Dosage | Toxicity | Cancer Indication |
|---|---|---|---|---|---|---|---|
| 4,4-dimethyl-2-phenyl-3-[4-(methylsulfonyl)phenyl]cyclobutenone; 1,2-diarylcyclobutenes | | Merck & Co | Cyclooxygenase 2 inhibitor | | | | |
| | | Chugai | Cyclooxygenase 2 inhibitor | WO 9730030 | | | |
| 2-(4-methoxyphenyl)-4-methyl-1-(4-sulfamoylphenyl)pyrrole; 1,2-diphenylpyrrole derivatives | | Sankyo | Cyclooxygenase 2 inhibitor | EP 799823 | | | |
| tetrahydrofuranones | | Bristol-Myers Squibb | Cyclooxygenase 2 inhibitor | WO 9737984 | | | |
| N-[5-(4-fluoro)phenoxy]thiophene-2-methanesulfonamide | RWJ-63556 | Johnson & Johnson | 5 Lipoxygenase inhibitor; Cyclooxygenase 2 inhibitor; Leucotriene B4 antagonist | | | | |
| 5(E)-(3,5-di-tert-butyl-4-hydroxy)benzylidene-2-ethyl-1,2-isothiazolidine-1,1-d ioxide | S-2474 | Shionogi | Prostaglandin E2 antagonist; Leucotriene B4 antagonist; Cyclooxygenase 2 inhibitor | EP 595546 | | | |
| | SC-57666 | Monsanto | Cyclooxygenase 2 inhibitor | | | | |
| 3-formylamino-7-methylsulfonylamino-6-phenoxy-4H-1-benzopyran-4-one | T-614 | Toyama | Cyclooxygenase 2 inhibitor; Interleukin 1b antagonist; Interleukin 6 antagonist | DE 3834204 | | | |
| Benzenesulfonamide, 4-(5-(4-methylphenyl)-3-(trifluoromethyl)-1H-pyrazol-1-yl)- | celecoxib; Celebrex; SC-58635; YM-177 | Monsanto | Cyclooxygenase 2 inhibitor | | | | |
| 2H-1,2-Benzothiazine-3-carboxamide, 4-hydroxy-2-methyl-N-(5-methyl-2-thiazolyl)-, 1,1-dioxide- | meloxicam; Mobic; Mobec; Moricox; Mobicox; Movalis; | Boehringer Ingelheim | Cyclooxygenase 2 inhibitor; Prostaglandin synthase inhibitor | U.S. Pat. No. 4233299 | 15–30 mg/day | | |
| Methanesulfonamide, N-(4-nitro-2-phenoxyphenyl) | nimesulide | Helsinn | Cyclooxygenase 2 inhibitor; Prostaglandin synthase inhibitor | U.S. Pat. No. 3840597 | | | |
| Methanesulfonamide, N-(4-nitro-2-phenoxyphentyl) | nimesulide, Poli | Poli | Cyclooxygenase 2 inhibitor | | | | |
| | valdecoxib | Monsanto | COX-2 inhibitor | U.S. Pat. No. 5,633,272 | | | |

TABLE 2

Preferred COX-2 Inhibitors

| Patent | Publication/issue/filing Dates | Oncology Indication | Dosage of Preferred Compounds |
|---|---|---|---|
| U.S. Pat. No. 5776967 A | 1998 July 07 | colorectal cancer | |
| WO 9821195 A1 | 1998 May 22 | colorectal cancer | |

TABLE 2-continued

Preferred COX-2 Inhibitors

| Patent | Publication/issue/filing Dates | Oncology Indication | Dosage of Preferred Compounds |
| --- | --- | --- | --- |
| WO 9804527 A1 | 1998 Feb. 05 | colorectal cancer | 0.01–100 mg/kg/day orally or parenterally |
| WO 9825896 A1 | 1998 June 18 | | |
| U.S. Pat. No. 5760068 A | 1998 June 02 | | |
| WO 9822101 A2 | 1998 May 28 | colorectal cancer | |
| WO 9816227 A1 | 1998 Apr. 23 | antiangiogenic | |
| U.S. Pat. No. 5719163 A | 1998 Feb. 17 | epithelial cell neoplasia | |
| WO 9806708 A1 | 1998 Feb. 19 | | |
| WO 9738986 A1 | 1997 Oct. 23 | | |
| U.S. Pat. No. 5663180 A | 1997 Sept. 02 | | |
| WO 9729776 A1 | 1997 Aug. 21 | | |
| WO 9729774 A1 | 1997 Aug. 21 | cancer | 0.1–2000 (preferably 0.5–500, especially 1–100) mg/kg/day orally, intravascularly, intraperitoneally, subcutaneously, intramuscularly, or topically. |
| WO 9729775 A1 | 1997 Aug. 21 | cancer | 0.1–2000 (preferably 0.5–500, especially 1–100) mg/kg/day orally, intravascularly, intraperitoneally, subcutaneously, intramuscularly, or topically. |
| WO 9727181 A1 | 1997 July 31 | | |
| WO 9714679 A2 | 1997 Apr. 24 | | |
| WO 9711704 A1 | 1997 Apr. 03 | | |
| U.S. Pat. No. 5616601 A | 1997 Apr. 01 | | |
| WO 9641645 A1 | 1996 Dec. 27 | | |
| WO 9641625 A1 | 1996 Dec. 27 | colorectal cancer | 0.01–100 mg/kg/day oral, topical or parenteral. |
| WO 9641626 A1 | 1996 Dec. 27 | | |
| WO 9638442 A1 | 1996 Dec. 05 | | |
| WO 9638418 A1 | 1996 Dec. 05 | colorectal cancer | 0.1–100 (preferably 0.1–10) mg/kg/day, orally, injection, topically, or transdermally. |
| WO 9625405 A1 | 1996 Aug. 22 | | |
| WO 9624585 A1 | 1996 Aug. 15 | | |
| WO 9609293 A1 | 1996 Mar. 28 | | |
| WO 9603387 A1 | 1996 Feb. 08 | | |
| U.S. Pat. No. 5739166 | 1998 Apr. 14 | colorectal cancer | 0.01–100 (preferably 0.1–10 mg/kg/day, orally, topical or intramuscular |
| WO 9616934 A1 | 1996 June 06 | | |
| WO 9603388 A1 | 1996 Feb. 08 | | |
| WO 9603392 A1 | 1996 Feb. 08 | | |
| WO 9530652 A1 | 1995 Nov. 16 | | |
| WO 9515316 A1 | 1995 June 08 | | |
| WO 9515318 A1 | 1995 June 08 | | |
| U.S. Pat. No. 5393790 A | 1995 Feb. 28 | | |
| U.S. Pat. No. 5380738 | 1995 Jan. 10 | colorectal cancer | 0.01–100 (pref. 0.1–50) mg/kg/day, oral, parental, or topical |
| WO 9427980 A1 | 1994 Dec. 08 | | |
| U.S. Pat. No. 5719163 | 1998 Feb. 17 | colorectal cancer | 0.01–100 (pref. 0.1–50) mg/kg/day, oral, parental, or topical |
| WO 9427980 A1 | 1994 Dec. 08 | | |
| U.S. Pat. No. 5420343 A | 1995 May 30 | | |
| U.S. Pat. No. 5434178 | 1995 July 18 | | |
| U.S. Pat. No. 5466823 | 1995 Nov. 14 | | |
| U.S. Pat. No. 5521207 | 1996 May 28 | | |
| U.S. Pat. No. 5563165 | 1996 Oct. 08 | | |
| U.S. Pat. No. 5508426 | 1996 Apr. 16 | | |
| U.S. Pat. No. 5504215 | 1996 Apr. 02 | | |
| U.S. Pat. No. 5516907 | 1996 May 14 | | |
| U.S. Pat. No. 5510496 | 1996 Apr. 23 | | |
| U.S. Pat. No. 5753688 | 1998 May 19 | | |
| U.S. Pat. No. 5753688 | 1998 May 19 | | |

TABLE 2-continued

Preferred COX-2 Inhibitors

| Patent | Publication/issue/filing Dates | Oncology Indication | Dosage of Preferred Compounds |
|---|---|---|---|
| U.S. Pat. No. 5736579 | 1998 Apr. 07 | colorectal cancer | |
| WO 9521817 A1 | 1995 Aug. 17 | | |
| SOFRC 95/1107 | 1996 Apr. 24 | | |
| U.S. Pat. No. 5668161 | 1997 Sept. 16 | | |
| U.S. Pat. No. 5418254 | 1995 May 23 | | |
| U.S. Pat. No. 5576339 | 1996 Nov. 19 | | colorectal cancer |
| U.S. Pat. No. 5672626 | 1997 Sept. 30 | | |
| U.S. Pat. No. 5670510 | 1997 Sept. 23 | | |
| U.S. Pat. No. 5686470 | 1997 Nov. 11 | colorectal cancer | 0.01–100 (preferably 0.1–10) mg/kg/day |
| WO 9624584 A1 | 1996 Aug. 15 | | |
| U.S. Pat. No. 5580985 | 1996 Dec. 03 | | 0.01–100 (preferably 0.1–10) mg/kg/day |
| WO 9603385 A1 | 1996 Feb. 08 | | |
| U.S. Pat. No. 5756530 | 1998 May 26 | | 0.01–100 (preferably 0.1–10) mg/kg/day |
| WO 9603385 A1 | 1996 Feb. 08 | | |
| U.S. Pat. No. 5486534 A | 1996 Jan. 23 | | |
| WO 9603385 A1 | 1996 Feb. 08 | | |
| U.S. Pat. No. 5620999 | 1997 Apr. 15 | colorectal cancer | 0.01–100 (preferably 0.5–20) mg/kg/day, oral, intravascular, intraperitoneal, subcutaneous, intramuscular, or topical |
| WO 9603387 A1 | 1996 Feb. 08 | | |
| U.S. Pat. No. 08/765,865 | 1997 Jan. 10 | | |
| U.S. Pat. No. 5696143 | 1997 Sept. 12 | | |
| WO 960923 A1 | 1996 Mar. 28 | | |
| U.S. Pat. No. 5547975 | 1996 Aug. 20 | | |
| WO 9609304 A1 | 1996 Mar. 28 | | |
| U.S. Pat. No. 08/809475 | 1997 June 09 | | |
| U.S. Pat. No. 5565482 | 1996 Oct. 15 | | |
| WO 9609304 A1 | 1996 Mar. 28 | | |
| U.S. Pat. No. 5670532 | 1997 Sept. 23 | | |
| WO 9609304 A1 | 1996 Mar. 28 | | |
| U.S. Pat. No. 5596008 | 1997 Jan. 21 | | |
| WO 9624585 A1 | 1996 Aug. 15 | | |
| U.S. Pat. No. 08/809318 | 1997 Mar. 20 | | |
| U.S. Pat. No. 08/849069 | 1997 Nov. 17 | | |
| U.S. Pat. No. 08/387680 | 1995 Feb. 13 | | |
| U.S. Pat. No. 08/894124 | 1997 Aug. 11 | | |
| U.S. Pat. No. 08/702417 | 1996 Aug. 14 | | |
| U.S. Pat. No. 08/801768 | 1997 Feb. 18 | | |
| U.S. Pat. No. 5643933 | 1997 July 01 | | |
| WO 9638442 A1 | 1996 Dec. 05 | | |
| U.S. Pat. No. 08/952661 | 1996 Apr. 20 | | |
| U.S. Pat. No. 08/945840 | 1996 May 31 | | |
| U.S. Pat. No. 08/822528 | 1997 Mar. 24 | | |
| U.S. Pat. No. 08/541850 | 1995 Oct. 10 | | |
| U.S. Pat. No. 08/540522 | 1995 Oct. 10 | | |
| PCT U.S. Pat. No. 97/05497 | 1997 Apr. 11 | | |
| U.S. Pat. No. 08/908554 | 1997 Aug. 08 | | |
| U.S. Pat. No. 09/005610 | 1998 Jan. 12 | | |
| U.S. Pat. No. 08/987356 | 1997 Dec. 09 | | |
| U.S. Pat. No. 60/032688 | 1996 Dec. 10 | | |
| PCT U.S. Pat. No. 98/07677 | 1998 Apr. 18 | | |
| U.S. Pat. No. 09/062537 | 1998 Apr. 17 | | |
| U.S. Pat. No. 60/044485 | 1997 Apr. 21 | | |
| U.S. Pat. No. 08/004/822 | 1993 Jan. 15 | | |
| U.S. Pat. No. 08/464722 | 1995 June 24 | | |
| U.S. Pat. No. 08/425022 | 1995 Apr. 13 | | |
| U.S. Pat. No. 08/425029 | 1995 Apr. 19 | | |
| U.S. Pat. No. 08/424979 | 1995 Apr. 19 | | |
| U.S. Pat. No. 08/969953 | 1997 Nov. 25 | | |
| U.S. Pat. No. 5380738 | 1995 Jan. 10 | | |
| U.S. Pat. No. 08/952156 | 1997 Nov. 11 | | |
| U.S. Pat. No. 08/647911 | 1996 May 30 | | |
| U.S. Pat. No. 08/457902 | 1995 June 01 | | |
| U.S. Pat. No. 08/957345 | 1997 Oct. 24 | | |
| EPO 95909447.5 | 1995 Feb. 07 | | |
| U.S. Pat. No. 08/776358 | 1997 Jan. 24 | | |
| U.S. Pat. No. 08/237739 | 1994 May 04 | | |
| U.S. Pat. No. 08/894102 | 1997 Aug. 08 | | |
| EPO 95928164.3 | 1995 July 27 | | |
| U.S. Pat. No. 09/101493 | 1998 July 09 | | |
| U.S. Pat. No. 08/992327 | 1997 Dec. 17 | | |
| U.S. Pat. No. 08/776090 | 1997 June 09 | | |

TABLE 2-continued

Preferred COX-2 Inhibitors

| Patent | Publication/issue/filing Dates | Oncology Indication | Dosage of Preferred Compounds |
|---|---|---|---|
| U.S. Pat. No. 08/765865 | 1997 Jan. 10 | | |
| AT 9700165 A | 1998 Apr. 15 | | |
| AU 9719132 A | 1997 Aug. 14 | | |
| CA 2164559 AA | 1996 June 10 | | |
| DE 19518421 A1 | 1996 Nov. 21 | | |
| DE 19533643 A1 | 1997 Mar. 13 | | 0.01–1000 mg/day orally or parenterally |
| DE 19533644 A1 | 1997 Mar. 13 | | 0.01–1000 mg/day orally or parenterally |
| EP 714895 A1 | 1996 June 05 | | 0.001–150 (preferably 5–20) mg/kg/day |
| EP 799823 A1 | 1997 Oct. 08 | | |
| EP 832652 A1 | 1998 Apr. 01 | adenocarcinoma | |
| EP 846689 A1 | 1998 June 10 | metastasis inhibitors | |
| EP 850894 A1 | 1998 July 01 | | |
| EP 850895 A1 | 1998 July 01 | | |
| FR 2751966 A1 | 1998 Feb. 06 | | Oral or parenteral 0.1–100 mg/kg/day. |
| GB 2283745 A1 | 1995 May 17 | | |
| GB 2294879 A1 | 1996 May 15 | | |
| GB 2319772 A | 1998 June 03 | cancer | 50 mg to 5 g/day |
| DE 19753463 A1 | 1998 June 04 | | (preferably 100–500 mg/day in 1 to 3 doses) |
| GB 2320715 A | 1998 July 01 | | |
| JP 08157361 A2 | 1996 June 18 | | |
| JP 09048769 A2 | 1997 Feb. 18 | | |
| JP 09071656 A2 | 1997 Mar. 18 | | |
| JP 09071657 A2 | 1997 Mar. 18 | | |
| JP 09077664 A2 | 1997 Mar. 25 | | |
| JP 09194354 A2 | 1997 July 29 | ulcerative colitis | |
| JP 09221422 A2 | 1997 Aug. 26 | | |
| JP 10175861 A2 | 1998 June 30 | metastasis inhibitors | |
| U.S. Pat. No. 5474995 A | 1995 Dec. 12 | | |
| U.S. Pat. No. 5510368 A | 1996 Apr. 23 | | 0.1–140 mg/kg/day or 0.5–7 g/patient, oral, topical, perenteral, inhalation, rectal |
| U.S. Pat. No. 5604260 A | 1997 Feb. 18 | | |
| U.S. Pat. No. 5616458 A | 1997 Apr. 01 | | |
| U.S. Pat. No. 5633272 A | 1997 May 27 | | |
| U.S. Pat. No. 5663195 A | 1997 Sept. 02 | | 0.01–100 mg/kg/day; 0.5 mg–6 g/day |
| U.S. Pat. No. 5677318 A | 1997 Oct. 14 | inhibitor of cellular neoplastic transformations and metastatic tumor growth; treatment of proliferative disorders, e.g., tumor angiogenesis | |
| U.S. Pat. No. 5677318 A | 1997 Oct. 14 | | |
| U.S. Pat. No. 5681842 A | 1997 Oct. 28 | | |
| U.S. Pat. No. 5686460 A | 1997 Nov. 11 | | |
| U.S. Pat. No. 5733909 A | 1998 Mar. 31 | | |
| U.S. Pat. No. 5783597 A | 1998 July 21 | | |
| WO 9413635 A1 | 1994 June 23 | | |
| WO 9414977 A1 | 1994 July 07 | | |
| WO 9420480 A1 | 1994 Sept. 15 | Inhibition of neoplastic transformations and metastatic tumor growth | 0.01–140 mg/kg/day adminstered orally. |
| WO 9426731 A1 | 1994 Nov. 24 | | |
| WO 9500501 A2 | 1995 Jan. 05 | | |
| WO 9511883 A1 | 1995 May 04 | colorectal cancer | |
| WO 9606840 A1 | 1996 Mar. 07 | | |
| WO 9608482 A1 | 1996 Mar. 21 | | |
| WO 9611676 A1 | 1996 Apr. 25 | | 0.01–140 mg/kg/day |
| WO 9612483 A1 | 1996 May 02 | inhibition of nitric oxide formation | |
| WO 9613483 A1 | 1996 May 09 | Inhibition of neoplastic transformation and metastatic tumor growth | 0.01–140 mg/kg/day |

TABLE 2-continued

Preferred COX-2 Inhibitors

| Patent | Publication/issue/filing Dates | Oncology Indication | Dosage of Preferred Compounds |
|---|---|---|---|
| WO 9619462 A1 | 1996 June 27 | | 0.01–1000 (preferably 0.1–300) mg/day p.o. or parenterally |
| WO 9619462 A1 | 1996 June 27 | | |
| WO 9619463 A1 | 1996 June 27 | | |
| WO 9619463 A1 | 1996 June 27 | | 0.1–1000 (preferably 1–300) mg/day p.o. or parenterally |
| WO 9619469 A1 | 1996 June 27 | | |
| WO 9621667 A1 | 1996 July 18 | | |
| WO 9623786 A1 | 1996 Aug. 08 | osteosarcoma | 0.01–140 mg/kg/day, orally, rectal, injection, topical. |
| WO 9624604 A1 | 1996 Aug. 15 | | |
| WO 9625405 A1 | 1996 Aug. 22 | | |
| WO 9625928 A1 | 1996 Aug. 29 | | |
| WO 9626921 A1 | 1996 Sept. 06 | | |
| WO 9631509 A1 | 1996 Oct. 10 | | |
| WO 9636617 A1 | 1996 Nov. 21 | colorectal cancer | |
| WO 9636623 A1 | 1996 Nov. 21 | | |
| WO 9637467 A1 | 1996 Nov. 28 | | 0.01–140 mg/kg/day, orally, topical, parenteral, rectal or inhalation. |
| WO 9637469 A1 | 1996 Nov. 28 | | |
| WO 9639144 A1 | 1996 Dec. 12 | | |
| WO 9640143 A1 | 1996 Dec. 19 | | |
| WO 9641626 A1 | 1996 Dec. 27 | colorectal cancer | |
| WO 9703667 A1 | 1997 Feb. 06 | colonic adenomas; colonic adenocarcinomas | |
| WO 9703953 A1 | 1997 Feb. 06 | | 0.01–1000 mg p.o or i.p. (oral, parenteral, rectal, topical or transdermal) |
| WO 9709977 A1 | 1997 Mar. 20 | | |
| WO 9710840 A1 | 1997 Mar. 27 | | |
| WO 9711701 A1 | 1997 Apr. 03 | cancer | |
| WO 9711701 A1 | 1997 Apr. 03 | | |
| WO 9713755 A1 | 1997 Apr. 17 | cancer | |
| WO 9713767 A1 | 1997 Apr. 17 | | |
| WO 9714691 A1 | 1997 Apr. 24 | | |
| WO 9716435 A1 | 1997 May 09 | | |
| WO 9725045 A1 | 1997 July 17 | | 0.1–80 mg/kg/day orally or parenterally |
| WO 9725046 A1 | 1997 July 17 | | |
| WO 9725047 A1 | 1997 July 17 | | 0.1–80 mg/kg/day oral or parenteral |
| WO 9725048 A1 | 1997 July 17 | pulmonary sarcoisosis | 0.1–80 mg/kg/day oral or parenteral |
| WO 9727181 A1 | 1997 July 31 | colorectal cancer | |
| WO 9728120 A1 | 1997 Aug. 07 | | |
| WO 9728121 A1 | 1997 Aug. 07 | | 0.01–140 mg/kg/day |
| WO 9730030 A1 | 1997 Aug. 21 | | 3–150 mg/hg p.o. or 1–50 mg/hg parenterally |
| WO 9731631 A1 | 1997 Sept. 04 | | |
| WO 9734882 A1 | 1997 Sept. 25 | colorectal cancer | |
| WO 9736497 A2 | 1997 Oct. 09 | antineoplastic; prostate, renal, colon, breast, or cervical cancer | |
| WO 9736863 A1 | 1997 Oct. 09 | | 0.01–140 mg/kg/day (oral, topical, rectal, parenteral, inhalation) |
| WO 9737984 A1 | 1997 Oct. 16 | | Orally 300 mg/kg/day |
| WO 9738686 A1 | 1997 Oct. 23 | regulation of COX-II expression | |
| WO 9740012 A1 | 1997 Oct. 30 | | |
| WO 9744027 A1 | 1997 Nov. 27 | | Orally 2.5–250 mg/day (preferably 12.5–20 mg/day) |
| WO 9744028 A1 | 1997 Nov. 27 | | |
| WO 9745420 A1 | 1997 Dec. 04 | | |
| WO 9746524 A1 | 1997 Dec. 11 | | |

TABLE 2-continued

Preferred COX-2 Inhibitors

| Patent | Publication/issue/filing Dates | Oncology Indication | Dosage of Preferred Compounds |
|---|---|---|---|
| WO 9746532 A1 | 1997 Dec. 11 | | 0.08–15.0 mg/kg/day (preferably 0.16–3.0 mg/kg/day) |
| WO 9800416 A1 | 1998 Jan. 08 | | |
| WO 9803484 A1 | 1998 Jan. 29 | Inhibit neoplastic formation and metastic tumor growth | Orally 0.01–140 mg/kg/day (preferably 0.5–7 mg/kg/day) |
| WO 9805639 A1 | 1998 Feb. 12 | | |
| WO 9806715 A1 | 1998 Feb. 19 | | |
| WO 9807425 A1 | 1998 Feb. 26 | | 0.01–80 mg/kg/day oral or parenteral; topical 0.1–150 mg/day in 1–4 doses. |
| WO 9807714 A1 | 1998 Feb. 26 | | |
| WO 9811080 A1 | 1998 Mar. 19 | | 1–1000 mg/day (oral, rectal, topical); 0.1–500 mg/day parenteral. |
| WO 9815528 A1 | 1998 Apr. 16 | | |
| WO 9816227 A1 | 1998 Apr. 23 | | |
| WO 9817292 A1 | 1998 Apr. 30 | | |
| WO 9821195 A1 | 1998 May 22 | tumor angiogenesis; colorectal cancers | |
| WO 9822101 A2 | 1998 May 28 | metastasis | |
| WO 9822104 A2 | 1998 May 28 | | |
| WO 9822442 A2 | 1998 May 28 | | |
| WO 9822457 A1 | 1998 May 28 | | |
| WO 9824782 A2 | 1998 June 11 | | |
| ZA 9704806 A | 1998 Mar. 25 | colon cancer | 0.1–500 mg/kg/day administered orally |
| WO98/57924 | | | |
| WO98/39330 | | | |
| WO98/41516 | | | |
| WO98/46594 | | | |
| WO98/47871 | | | |
| WO98/47890 | | | |
| WO99/18960 | | | |
| WO99/23087 | | | |
| WO99/24025 | | | |
| WO99/15503 | | | |
| WO99/14195 | | | |
| WO99/14194 | | | |
| WO99/05104 | | | |
| WO99/12930 | | | |
| WO99/10332 | | | |
| WO99/10331 | | | |
| WO99/11605 | | | |
| WO99/33796 | | | |
| WO99/35130 | | | |
| WO99/15505 | | | |
| U.S. Pat. No. 5,916,905 | | | |
| U.S. Pat. No. 5,830,911 | | | |
| U.S. Pat. No. 5,840,924 | | | |
| U.S. Pat. No. 5,849,943 | | | |
| U.S. Pat. No. 5,869,524 | | | |
| U.S. Pat. No. 5,869,524 | | | |
| U.S. Pat. No. 5,859,257 | | | |
| U.S. Pat. No. 5,859,036 | | | |
| U.S. Pat. No. 5,883,267 | | | |
| U.S. Pat. No. 5,863,946 | | | |
| U.S. Pat. No. 5,811,425 | | | |
| U.S. Pat. No. 5,908,858 | | | |
| U.S. Pat. No. 5,908,852 | | | |
| U.S. Pat. No. 5,919,809 | | | |
| U.S. Pat. No. 5,922,742 | | | |
| WO 94/15932 | 21 July 1994 | | |
| WO 95/09238 | 6 Apr. 1995 | | |
| WO 95/18799 | 13 July 1995 | | |
| WO 96/06840 | 7 Mar. 1996 | | |
| WO 96/37468 | 28 Nov. 1996 | | |
| WO 96/42941 | 10 July 1996 | | |
| WO 98/43966 | 8 Oct. 1998 | | |
| WO 98/41511 | 24 Sept. 1998 | | |
| U.S. Pat. No. 5,409,944 | 25 Apr. 1995 | | |
| U.S. Pat. No. 5,521,213 | 28 May 1996 | | |
| U.S. Pat. No. 5,536,752 | 16 July 1996 | | |

TABLE 2-continued

Preferred COX-2 Inhibitors

| Patent | Publication/issue/filing Dates | Oncology Indication | Dosage of Preferred Compounds |
|---|---|---|---|
| U.S. Pat. No. 5,550,142 | 27 Aug. 1996 | | |
| U.S. Pat. No. 5,552,422 | 3 Sept. 1996 | | |
| U.S. Pat. No. 5,604,253 | 18 Feb. 1997 | | |
| U.S. Pat. No. 5,639,780 | 17 June 1997 | | |
| U.S. Pat. No. 5,691,374 | 25 Nov. 1997 | | |
| U.S. Pat. No. 5,698,584 | 16 Dec. 1997 | | |
| U.S. Pat. No. 5,767,291 | 16 June 1998 | | |
| U.S. Pat. No. 5,789,413 | 4 Aug. 1998 | | |
| U.S. Pat. No. 5,932,598 | 3 Aug. 1999 | | |
| U.S. Pat. No. 5,932,994 | 3 Aug. 1999 | | |

Preferred Combinations Generally

A preferred combination therapy consists essentially of a COX-2 inhibitor in combination with a radiotherapeutic agent.

Examples of COX-2 inhibitors that may be used in the combination therapy are provided in, but not limited to, Table No. 1. Preferred COX-2 inhibitors that may be used in the combination therapy are shown in Table No. 2. The most preferred COX-2 inhibitors are selected from the group consisting of:

1)
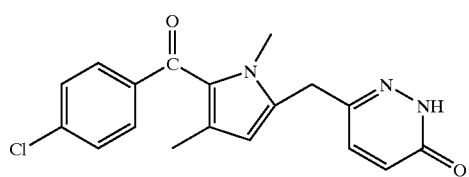

2)
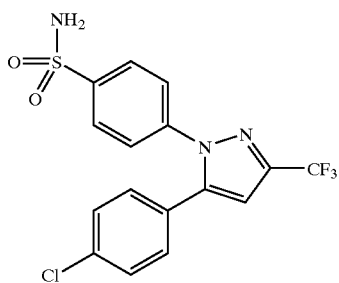

3)
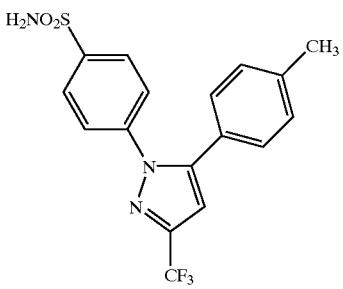

4)
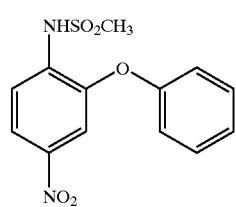

5)
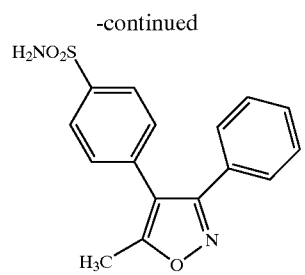

6)
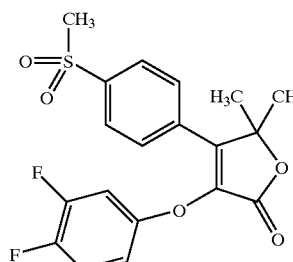

7)
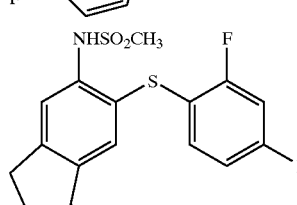

8)
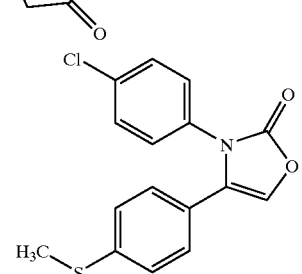

9)
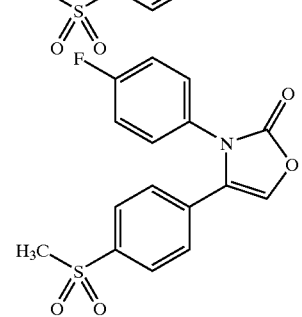

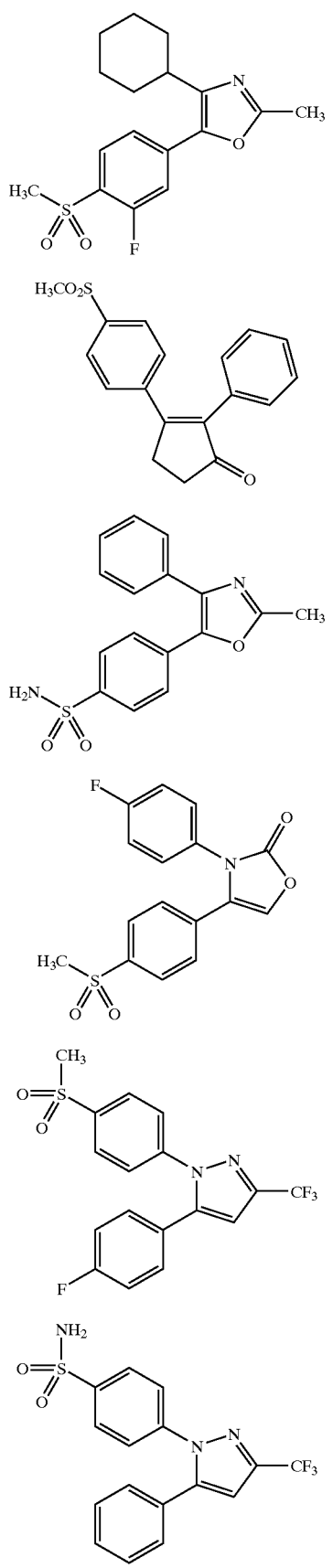
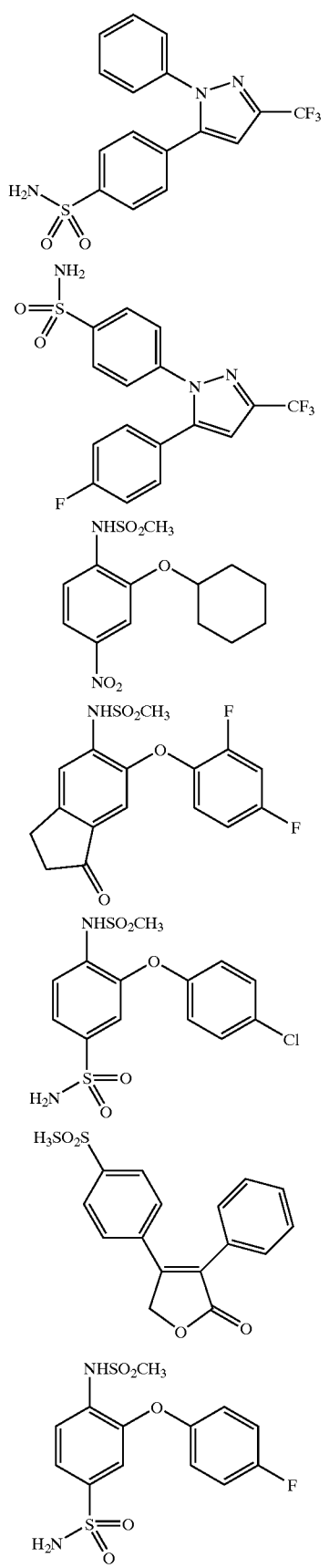

23) 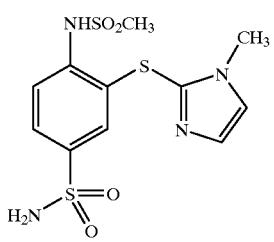
24) 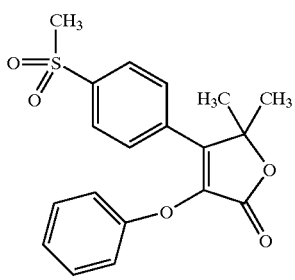
25) 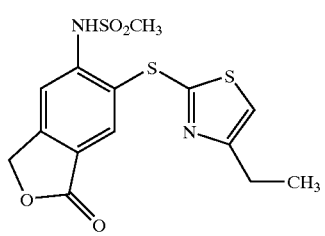
26) 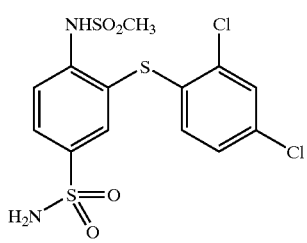
27) 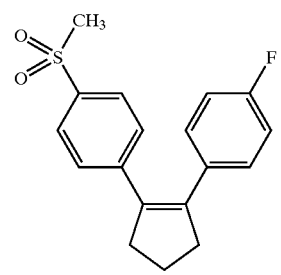
28) 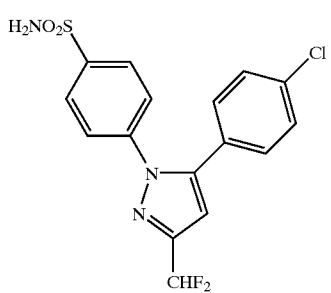
29) 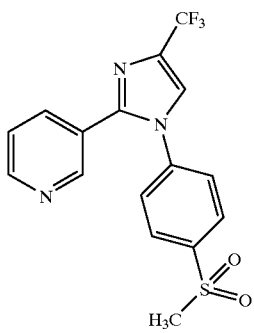
30) 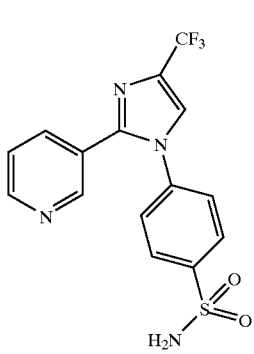
31) 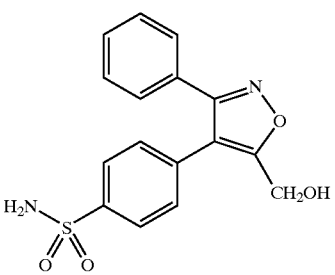
32) 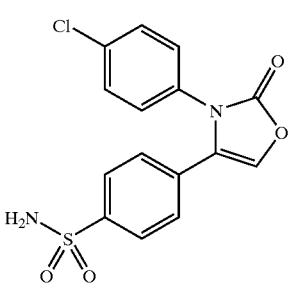
33) 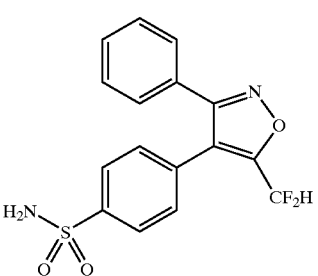

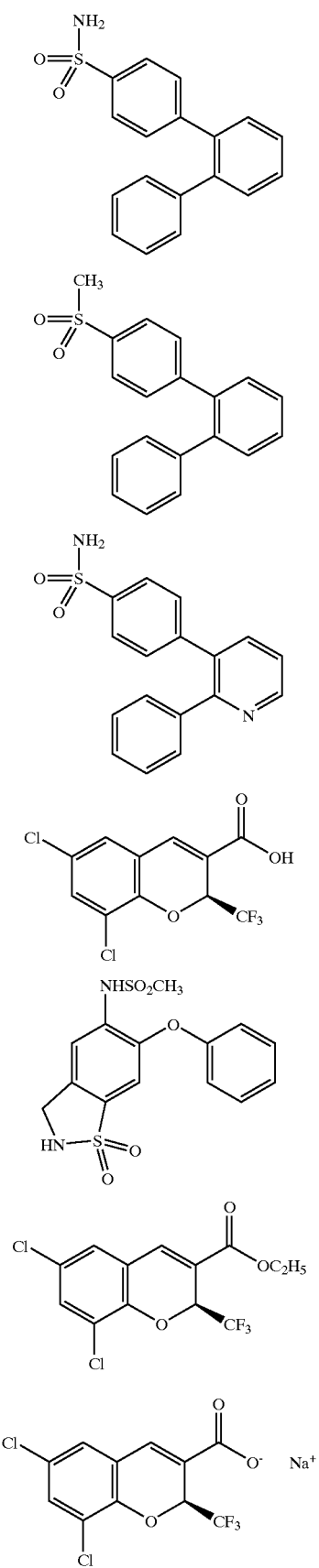

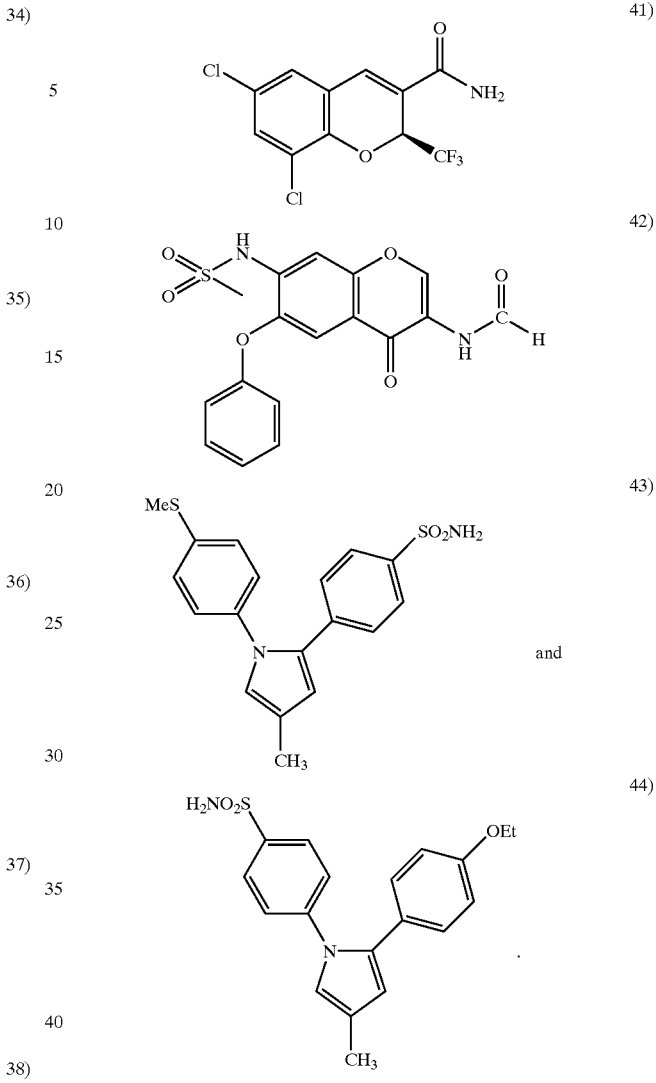

COX-2 Inhibitors

Specific COX-2 inhibitors are useful for the treatment of cancer (WO98/16227) and in several animal models reduce angiogenesis driven by various growth factors (WO98/22101). Anti-angiogenesis was achieved with a COX-2 inhibitor in rats implanted with bFGF, vascular endothelium growth factor (VEGF) or carrageenan, proteins with well-known angiogenic properties. (Masferrer, et al., 89th Annual Meeting of the American Association for Cancer Research, March 1998.)

Dosage of COX-2 Inhibitors

Dosage levels of COX-2 inhibitors on the order of about 0.1 mg to about 10,000 mg of the active antiangiogenic ingredient compound are useful in the treatment of the above conditions, with preferred levels of about 1.0 mg to about 1,000 mg. The amount of active ingredient that may be combined with other anticancer agents to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of cancers in accordance with the present invention. In terms of treatment protocols, it should be appreciated that the dosage to be administered will depend on several factors, including the particular agent that is administered, the route administered, the condition of the particular patient, etc. Generally speaking, one will desire to administer an amount of the compound that is effective to achieve a serum level commensurate with the concentrations found to be effective in vitro. Thus, where an compound is found to demonstrate in vitro activity at, e.g., 10 $\mu$M, one will desire to administer an amount of the drug that is effective to provide about a 10 $\mu$M concentration in vivo. Determination of these parameters are well within the skill of the art.

These considerations, as well as effective formulations and administration procedures are well known in the art and are described in standard textbooks.

Administration Regimen

Any effective treatment regimen can be utilized and readily determined and repeated as necessary to effect treatment. In clinical practice, the compositions containing a COX-2 inhibitor alone or in combination with other therapeutic agents are administered in specific cycles until a response is obtained.

For patients who initially present without advanced or metastatic cancer, a COX-2 inhibitor in combination with radiation therapy, is used as a continuous post-treatment therapy in patients at risk for recurrence or metastasis (for example, in adenocarcinoma of the prostate, risk for metastasis is based upon high PSA, high Gleason's score, locally extensive disease, and/or pathological evidence of tumor invasion in the surgical specimen). The goal in these patients is to inhibit the growth of potentially metastatic cells from the primary tumor during surgery and inhibit the growth of tumor cells from undetectable residual primary tumor.

For patients who initially present with advanced or metastatic cancer, a COX-2 inhibitor in combination with radiation therapy of the present invention is used as a continuous supplement to, or possible replacement for hormonal ablation. The goal in these patients is to slow or prevent tumor cell growth from both the untreated primary tumor and from the existing metastatic lesions.

The following discussion highlights some agents in this respect, which are illustrative, not limitative. A wide variety of other effective agents also may be used.

Colorectal Cancer

The preferred combination therapy for the treatment of colorectal cancer is surgery, followed by a regimen of one or more chemotherapeutic agents, cycled over a one year time period. In the treatment of colorectal cancer, radiation alone or in combination with surgery and/or chemotherapeutic agents is often used. Preferred chemotherapeutic agents include fluorouracil, and Levamisole. Preferably, fluorouracil and Levamisole are used in combination.

Prostate Cancer

Current therapies for prostate cancer focus upon reducing levels of dihydrotestosterone to decrease or prevent growth of prostate cancer. Radiation alone or in combination with surgery and/or chemotherapeutic agents is often used.

Pancreas Cancer

Preferred combinations of therapy for the treatment of non-metastatic adenocarcinoma include the use of preoperative bilary tract decompression (patients presenting with obstructive jaundice); surgical resection, including standard resection, extended or radial resection and distal pancreatectomy (tumors of body and tail); adjuvant radiation; and chemotherapy. For the treatment of metastatic adenocarcinoma, the preferred chemotherapy consists of 5-fluorouracil, followed weekly cisplatin therapy.

Lung Cancer

In many countries including Japan, Europe and America, the number of patients with lung cancer is fairly large and continues to increase year after year and is the most frequent cause of cancer death in both men and women. Although there are many potential causes for lung cancer, tobacco use, and particularly cigarette smoking, is the most important. Additionally, etiologic factors such as exposure to asbestos, especially in smokers, or radon are contributory factors. Also occupational hazards such as exposure to uranium have been identified as an important factor. Finally, genetic factors have also been identified as another factor that increase the risk of cancer.

Lung cancers can be histologically classified into non-small cell lung cancers (e.g. squamous cell carcinoma (epidermoid), adenocarcinoma, large cell carcinoma (large cell anaplastic), etc.) and small cell lung cancer (oat cell). Non-small cell lung cancer (NSCLC) has different biological properties and responses to chemotherapeutics from those of small cell lung cancer (SCLC). Thus, chemotherapeutic formulas and radiation therapy are different between these two types of lung cancer.

Non-Small Cell Lung Cancer

Where the location of the non-small cell lung cancer tumor can be easily excised (stage I and II disease) surgery is the first line of therapy and offers a relatively good chance for a cure. However, in more advanced disease (stage IIIa and greater), where the tumor has extended to tissue beyond the bronchopulmonary lymph nodes, surgery may not lead to complete excision of the tumor. In such cases, the patient's chance for a cure by surgery alone is greatly diminished. Where surgery will not provide complete removal of the NSCLC tumor, other types of therapies must be utilized.

Today radiation therapy is the standard treatment to control unresectable or inoperable NSCLC. Improved results have been seen when radiation therapy has been combined with chemotherapy, but gains have been modest and the search continues for improved methods of combining modalities.

Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. A prefered course of treatment for a patient undergoing radiation therapy for NSCLC will be a treatment schedule over a 5 to 6 week period, with a total dose of 50 to 60 Gy administered to the patient in a single daily fraction of 1.8 to 2.0 Gy, 5 days a week. A Gy is an abbreviation for Gray and refers to 100 rad of dose.

However, as NSCLC is a systemic disease, and radiation therapy is a local modality, radiation therapy as a single line of therapy is unlikely to provide a cure for NSCLC, at least for those tumors that have metastasized distantly outside the zone of treatment. Thus, the use of radiation therapy with other modality regimens have important beneficial effects for the treatment of NSCLC.

Generally, radiation therapy has been combined temporally with chemotherapy to improve the outcome of treatment. There are various terms to describe the temporal relationship of administering radiation therapy and chemotherapy, and the following examples are the preferred treatment regimens and are generally known by those skilled in the art and are provided for illustration only and are not intended to limit the use of other combinations. "Sequential" radiation therapy and chemotherapy refers to the administration of chemotherapy and radiation therapy separately in time in order to allow the separate administration of either chemotherapy or radiation therapy. "Concomitant" radiation therapy and chemotherapy refers to the administration of chemotherapy and radiation therapy on the same day. Finally, "alternating" radiation therapy and chemotherapy refers to the administration of radiation therapy on the days in which chemotherapy would not have been administered if it was given alone.

It is reported that advanced non-small cell lung cancers do not respond favorably to single-agent chemotherapy and useful therapies for advanced inoperable cancers have been limited. (J. Clin. Oncol. 1992, 10, 829–838).

Japanese Patent Kokai 5-163293 refers to 16-membered-ring macrolide antibiotics as a drug delivery carrier capable of transporting anthoracycline-type anticancer drugs into the lungs for the treatment of lung cancers. However, the macrolide antibiotics specified herein are disclosed to be only a drug carrier, and there is no reference to the therapeutic use of macrolides against non-small cell lung cancers.

WO 93/18652 refers to the effectiveness of the specified 16-membered-ring macrolides such as bafilomycin, etc. in treating non-small cell lung cancers, but they have not yet been clinically practicable.

Pharmacology, vol. 41, pp. 177–183 (1990) describes that a long-term use of erythromycin increases productions of interleukins 1, 2 and 4, all of which contribute to host immune responses, but there is no reference to the effect of this drug on non-small cell lung cancers.

Tetragenesis, Carcinogenesis, and Mutagenesis, vol. 10, pp. 477–501 (1990) describes that some of antimicrobial drugs can be used as an anticancer agent, but does not refer to their application to non-small cell lung cancers.

In addition, interleukins are known to have an antitumor effect, but have not been reported to be effective against non-small cell lung cancers.

Any 14- or 15-membered-ring macrolides have not been reported to be effective against non-small cell lung cancers.

However, several chemotherapeutic agents have been shown to be efficacious against NSCLC. Preferred chemotherapeutic agents against NSCLC include etoposide, carboplatin, methotrexate, 5-fluorouracil, epirubicin, doxorubicin, and cyclophosphamide. The most preferred chemotherapeutic agents active against NSCLC include cisplatin, ifosfamide, mitomycin C, epirubicin, vinblastine, and vindesine.

Other agents that are under investigation for use against NSCLC include: camptothecins, a topoisomerase 1 inhibitor; navelbine (vinorelbine), a microtubule assebly inhibitor; taxol, inhibitor of normal mitotic activity; gemcitabine, a deoxycytidine analogue; fotemustine, a nitrosourea compound; and edatrexate, a antifol.

The overall and complete response rates for NSCLC has been shown to increase with use of combination chemotherapy as compared to single-agent treatment. Haskel, Chest. 1991, 99: 1325; Bakowsk, *Cancer Treat. Rev.* 1983, 10:159; Joss, *Cancer Treat. Rev.* 1984, 11: 205.

Small Cell Lung Cancer

Approximately 15 to 20 percent of all cases of lung cancer reported worldwide is small cell lung cancer (SCLC). (Ihde, *Cancer* 1984, 54, 2722). Currently, treatment of SCLC incorporates multi-modal therapy, including chemotherapy, radiation therapy and surgery. Response rates of localized or disseminated SCLC remain high to systemic chemotherapy, however, persistence of the primary tumor and persistence of the tumor in the associated lymph nodes has led to the integration of several therapeutic modalities in the treatment of SCLC.

The most preferred chemotherapeutic agents against SCLC include vincristine, cisplatin, carboplatin, cyclophosphamide, epirubicin (high dose)., etoposide (VP-16) I.V., etoposide (VP-16) oral, isofamide, teniposide (VM-26), and doxorubicin. Preferred single-agents chemotherapeutic agents include BCNU (carmustine), vindesine, hexamethylmelamine (altretamine), methotrexate, nitrogen mustard, and CCNU (lomustine). Other chemotherapeutic agents under investigation that have shown activity againe SCLC include iroplatin, gemcitabine, lonidamine, and taxol. Single-agent chemotherapeutic agents that have not shown activity against SCLC include mitoguazone, mitomycin C, aclarubicin, diaziquone, bisantrene, cytarabine, idarubicin, mitomxantrone, vinblastine, PCNU and esorubicin.

The poor results reported from single-agent chemotherapy has led to use of combination chemotherapy.

Additionally, radiation therapy in conjunction with the preferred combinations of angiogenesis inhibitors and systemic chemotherapy is contemplated to be effective at increasing the response rate for SCLC patients. The typical dosage regimen for radiation therapy ranges from 40 to 55 Gy, in 15 to 30 fractions, 3 to 7 times week. The tissue volume to be irradiated is determined by several factors and generally the hilum and subcarnial nodes, and bialteral mdiastinal nodes up to the thoraic inlet are treated, as well as the primary tumor up to 1.5 to 2.0 cm of the margins.

Breast Cancer

Today, among women in the United States, breast cancer remains the most frequent diagnoses cancer. One in 8 women in the United States at risk of developing breast cancer in their lifetime. Age, family history, diet, and genetic factors have been identified as risk factors for breast cancer. Breast cancer is the second leading cause of death among women.

Different chemotherapeutic agents are known in the art for treating breast cancer. Cytoxic agents used for treating breast cancer include doxorubicin,cyclophosphamide, methotrexate, 5-fluorouracil, mitomycin C, mitoxantrone, taxol, and epirubicin. (CANCER SURVEYS, Breast Cancer volume 18, Cold Spring Harbor Laboratory Press, 1993).

In the treatment of locally advanced non-inflammatory breast cancer, a COX-2 inhibitor and radiation therapy can be used to treat the disease in combination with other antiangiogenic agents, or in combination with surgery, or with chemotherapeutic agents. Preferred combinations of chemotherapeutic agents, and surgery that can be used in combination with the radiation therapy and COX-2 inhibitors include, but are not limited to: 1) doxorubicin, vincristine; 2) cyclophosphamide, doxorubicin, 5-flourouracil, vincristine, prednisone; 3) cyclophosphamide, doxorubicin, 5-flourouracil, premarin, tamoxifen; 4) cyclophosphamide, doxorubicin, 5-flourouracil, premarin, tamoxifen, mastectomy; 5) mastectomy, levamisole; 6) mastectomy; and 7) mastecomy, cyclophosphamide, doxorubicin, 5-fluorouracil, tamoxifen, halotestin.

In the treatment of locally advanced inflammatory breast cancer, COX-2 inhibitors and radiation therapy can be used to treat the disease in combination with other antiangiogenic agents, or in combination with surgery, or with chemotherapeutic agents. Preferred combinations of chemotherapeutic agents, radiation therapy and surgery that can be used in combination with the COX-2 inhibitors and radiation include, but or not limited to: 1) cyclophosphamide, doxorubicin, 5-fluorouracil; 2) cyclophosphamide, doxorubicin, 5-fluorouracil, mastectomy; 3) 5-flurouracil, doxorubicin, clyclophosphamide, vincristine, prednisone, mastectomy; 4) 5-flurouracil, doxorubicin, clyclophosphamide, vincristine, mastectomy; 5) cyclophosphamide, doxorubicin, 5-fluorouracil, vincristine; 6) cyclophosphamide, doxorubicin, 5-fluorouracil, vincristine, mastectomy; 7) doxorubicin, vincristine, methotrexate, followed by vincristine, cyclophosphamide, 5-florouracil; 8) doxorubicin, vincristine, cyclophosphamide, methotrexate, 5-florouracil, followed by vincristine, cyclophosphamide, 5-florouracil; 9) surgery, followed by cyclophosphamide, methotrexate, 5-fluorouracil, predinsone, tamoxifen, followed by cyclophosphamide, methotrexate, 5-fluorouracil, predinsone, tamoxifen, doxorubicin, vincristine, tamoxifen; 10) surgery, followed by cyclophosphamide, methotrexate, 5-fluorouracil, followed by cyclophosphamide, methotrexate, 5-fluorouracil, predinsone, tamoxifen, doxorubicin, vincristine, tamoxifen; 11) surgery, followed by cyclophosphamide, methotrexate, 5-fluorouracil, predinsone, tamoxifen, followed by cyclophosphamide, methotrexate, 5-fluorouracil, doxorubicin, vincristine, tamoxifen;; 12) surgery, followed by cyclophosphamide, methotrexate, 5-fluorouracil, followed by cyclophosphamide, methotrexate, 5-fluorouracil, predinsone, tamoxifen, doxorubicin, vincristine; 13) surgery, followed by cyclophosphamide, methotrexate, 5-fluorouracil, predinsone, tamoxifen, followed by cyclophosphamide, methotrexate, 5-fluorouracil, predinsone, tamoxifen, doxorubicin, vincristine, tamoxifen; 14) surgery, followed by cyclophosphamide, methotrexate, 5-fluorouracil, followed by cyclophosphamide, methotrexate, 5-fluorouracil, predinsone, tamoxifen, doxorubicin, vincristine; 15) surgery, followed by cyclophosphamide, methotrexate, 5-fluorouracil, predinsone, tamoxifen, followed by cyclophosphamide, methotrexate, 5-fluorouracil, doxorubicin, vincristine; 16) 5-florouracil, doxorubicin, cyclophosphamide followed by mastectomy, followed by 5-florouracil, doxorubicin, cyclophosphamide.

In the treatment of metastatic breast cancer, radiation therapy and COX-2 inhibitors are used to treat the disease in combination with surgery, or with chemotherapeutic agents. Preferred combinations of chemotherapeutic agents, and surgery that can be used in combination with the radiation therapy and COX-2 inhibitors include, but are not limited to: 1) cyclosphosphamide, methotrexate, 5-fluorouracil; 2) cyclophosphamide, adriamycin, 5-fluorouracil; 3) cyclosphosphamide, methotrexate, 5-flurouracil, vincristine, prednisone; 4) adriamycin, vincristine; 5) thiotepa, adriamycin, vinblastine; 6) mitomycin, vinblastine; 7) cisplatin, etoposide.

Bladder Cancer

The classification of bladder cancer is divided into three main classes: 1) superficial disease, 2) muscleinvasive disease, and 3) metastatic disease.

Currently, transurethral resection (TUR), or segmental resection, account for first line therapy of superficial bladder cancer, i.e., disease confined to the mucosa or the lamina propria. However, intravesical therapies are necessary, for example, for the treatment of high-grade tumors, carcinoma in situ, incomplete resections, recurrences, and multifocal papillary. Recurrence rates range from up to 30 to 80 percent, depending on stage of cancer.

Therapies that are currently used as intravesical therapies include chemotherapy, immuontherapy, bacille Calmette-Guerin (BCG) and photodynamic therapy. The main objective of intravesical therapy is twofold: to prevent recurrence in high-risk patients and to treat disease that cannot by resected. The use of intravesical therapies must be balanced with its potentially toxic side effects. Additionally, BCG requires an unimpaired immune system to induce an antitumor effect. Chemotherapeutic agents that are known to be inactive against superficial bladder cancer include Cisplatin, actinomycin D, 5-fluorouracil, bleomycin, and cyclophosphamide methotrxate.

In the treatment of superficial bladder cancer, COX-2 inhibitors and radiation therapy are used to treat the disease in combination with surgery (TUR), and intravesical therapies.

Preferred combinations of chemotherapeutic agents are selected from the group consisting of thiotepa (30 to 60 mg/day), mitomycin C (20 to 60 mg/day), and doxorubicin (20 to 80 mg/day).

The preferred intravesicle immunotherapuetic agent that may be used in the present invention is BCG. The preferred daily dose ranges from 60 to 120 mg, depending on the strain of the live attenuated tuberculosis organism used.

The preferred photodynamic therapuetic agent that may be used with the present invention is Photofrin I, a photosensitizing agent, administered intravenously. It is taken up by the low-density lipoprotein receptors of the tumor cells and is activated by exposure to visible light. Additionally, neomydium YAG laser activation generates large amounts of cytotoxic free radicals and singlet oxygen.

In the treatment of muscle-invasive bladder cancer, radiation therapy and COX-2 inhibitors can be used to treat the disease in combination with other antiangiogenic agents, or in combination with surgery (TUR), intravesical chemotherapy, and radical cystectomy with pelvic lymph node dissection.

The preferred radiation dose is between 5,000 to 7,000 cGY in fractions of 180 to 200 cGY to the tumor. Additionally, 3,500 to 4,700 cGY total dose is administered to the normal bladder and pelvic contents in a four-field technique. Radiation therapy should be considered only if the patient is not a surgical candidate, but may be considered as preoperative therapy.

The preferred combination of chemotherapeutic agents that can be used in combination with radiation therapy and the COX-2 inhibitors is cisplatin, methotrexate, vinblastine.

Currently no curative therapy exists for metastatic bladder cancer. The present invention contemplates an effective treatment of bladder cancer leading to improved tumor inhibition or regression, as compared to current therapies.

In the treatment of metastatic bladder cancer, a combination of radiation therapy and COX-2 inhibitors can be used to treat the disease in combination with surgery, or with chemotherapeutic agents.

Preferred combinations of chemotherapeutic agents include, but are not limited to: 1) cisplatin and methotrexate; 2) doxorubicin, vinblastine, cyclophoshamide, and 5-fluorouracil; 3) vinblastine, doxorubicin, cisplatin, methotrexate; 4) vinblastine, cisplatin, methotrexate; 5) cyclophosphamide, doxorubicin, cisplatin; 6) 5-fluorouracil, cisplatin.

Head and Neck Cancers

Head and neck cancer accounts for approximately 2% of new cancer cases in the United States. Common intracranial neoplasms include glioma, meningioma, neurinoma, and adenoma.

Preferred combinations that can be used along with a combination of radiation therapy and a COX-2 inhibitor for the treatment of malignant glioma include: 1) BCNU (carmustine); 2) methyl CCNU (lomustine); 3) medrol; 4) procarbazine; 5) BCNU, medrol; 6) misonidazole, BCNU; 7) streptozotocin; 8) BCNU, procarbazine; 9) BCNU, hydroxyurea, procarbazine, VM-26; 10) BNCU, 5-flourouacil; 11) methyl CCNU, dacarbazine; 12) misonidazole, BCNU; and 13) PCNU. The preferred dose of radiation therapy is about 5,500 to about 6,000 cGY. Preferred radiosensitizers include misonidazole, intra-arterial Budr and intravenous iododeoxyuridine (IUdR).

Biological Evaluation

NFSA tumor

The NFSA sarcoma is a nonimmunogenic and prostaglandin producing tumor that spontaneously developed in C3Hf/Kam mice. It exhibits an increased radioresponse if indomethacin is given prior to tumor irradiation. The NFSA tumor is relatively radioresistant and is strongly infiltrated by inflammatory mononuclear cells, primarily macrophages which secrete factors that stimulate tumor cell proliferation. Furthermore, this tumor produces a number of prostaglandins, including prostaglandin $E_2$ and prostaglandin $I_2$ Solitary tumors were generated in the right hind legs of mice by the injection of $3 \times 10^5$ viable NFSA tumor cells. Treatment with a COX-2 inhibitor (6 mg/kg body weight) or vehicle (0.05% Tween 20 and 0.95% polyethylene glycol) given in the drinking water was started when tumors were approximately 6 mm in diameter and the treatment was continued for 10 consecutive days. Water bottles were changed every 3 days. In some experiments, tumor irradiation was performed 3–8 days after initiation of the treatment with a COX-2 inhibitor. The end points of the treatment were tumor growth delay (days) and $TCD_{50}$ (tumor control dose 50, defined as the radiation dose yielding local tumor cure in 50% of irradiated mice 120 days after irradiation). To obtain tumor growth curves, three mutually orthogonal diameters of tumors were measured daily with a vernier caliper, and the mean values were calculated. In FIG. 1, which plots the growth of tumor treated with vehicle (o) or COX-2 inhibitor (•), the groups consisted of eight mice each, respectively. Treatment of mice with a COX-2 inhibitor alone significantly inhibited tumor growth.

Figure 2:
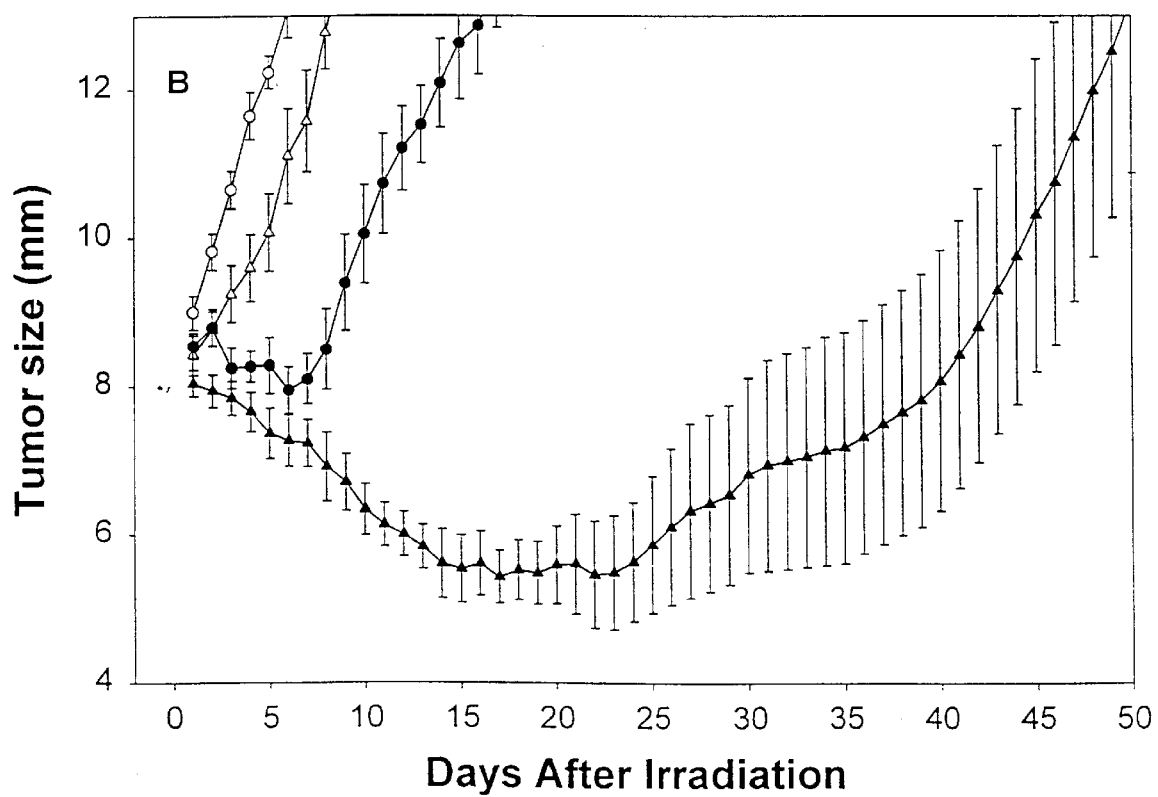
FIG. 2 shows the effect of a COx-2 inhibitor (4-[5-(4-chlorophenyl)-3-trifluoromethyl-1H-pyrazol-1-yl] benzenesulfonamide) in combination with local tumor irradiation on tumor growth.

Local tumor irradiation with single γ-ray doses of 30, 40, or 50 Gy was given when these tumors reached 8 mm in diameter. Irradiation to the tumor was delivered from a dual-source $^{137}$Cs irradiator at a dose rate of 6.31 Gy/minute. During irradiation, unanesthetized mice were immobilized on a jig and the tumor was centered in a circular radiation field 3 cm in diameter. Regression and regrowth of tumors were followed at 1–3 day intervals until the tumor diameter reached approximately 14 mm. FIG. 2 plots the growth curves to illustrate the effect of a COX-2 inhibitor on tumor growth when combined with a radiation dose of 30 Gy. Day 0 designates the time of tumor irradiation; it should be noted, however, that tumors in the groups receiving a COX-2 inhibitor reached the size of 8 mm (day 0) at a later time than tumors treated with the vehicle. Groups consisted of five to eight mice each. Two of eight mice in the COX-2 inhibitor only group died of unknown causes. (O=vehicle, Δ=COX-2 inhibitor, •=30 Gy, and ▲=COX-2 inhibitor plus 30 Gy). Vertical bars represent 95% confidence intervals.

Tumor diameter doubling time, based on tumor growth from 6 to 12 mm in diameter, was increased from 7.3 days (95% confidence interval [CI]=6.48.1 days) to 14.8 days (95% CI–11.5–18.1 days) (P<0.0001). The effect of a COX-2 inhibitor was evident already within 1 day from the start of the treatment.

The magnitude of tumor growth delay as a function of radiation dose with or without treatment with a COX-2 inhibitor was plotted (FIG. 3) to determine the enhancement of tumor response to radiation. This requires that tumor growth delay after radiation be expressed only as the absolute tumor growth delay, i.e., the time in days for tumors treated with radiation to grow from 8 to 12 mm in diameter minus the time in days for untreated tumors to reach the same size. It also requires that the effect of the combined a COX-2 inhibitor plus-radiation treatment be expressed as the normalized tumor growth delay. Normalized tumor growth delay is defined as the time for tumors treated with both a COX-2 inhibitor and radiation to grow from 8 to 12 mm in diameter minus the time in days for tumors treated with a COX-2 inhibitor alone to reach the same size. Absolute tumor growth delay and normalized tumor growth delay along with their 95% confidence intervals were plotted for all three radiation doses used in this experiment (30, 40, and 50 Gy). The enhancement factor was 3.64 (95% confidence interval 3.42–3.86), obtained by use of a likelihood analysis, to fit the ratio of the slopes of the two lines. While no tumors were cured by any of the three radiation doses given alone, tumors in one of six, in two of six, and in one of eight animals were cured when a COX-2 inhibitor treatment was combined with radiation treatment at 30, 40, and 50 Gy, respectively. Two of eight mice in the group that received the COX-2 inhibitor plus 40 Gy died of unknown causes. The mice whose tumors were cured and the mice that died were not included in tumor growth delay analysis.

Figure 3:
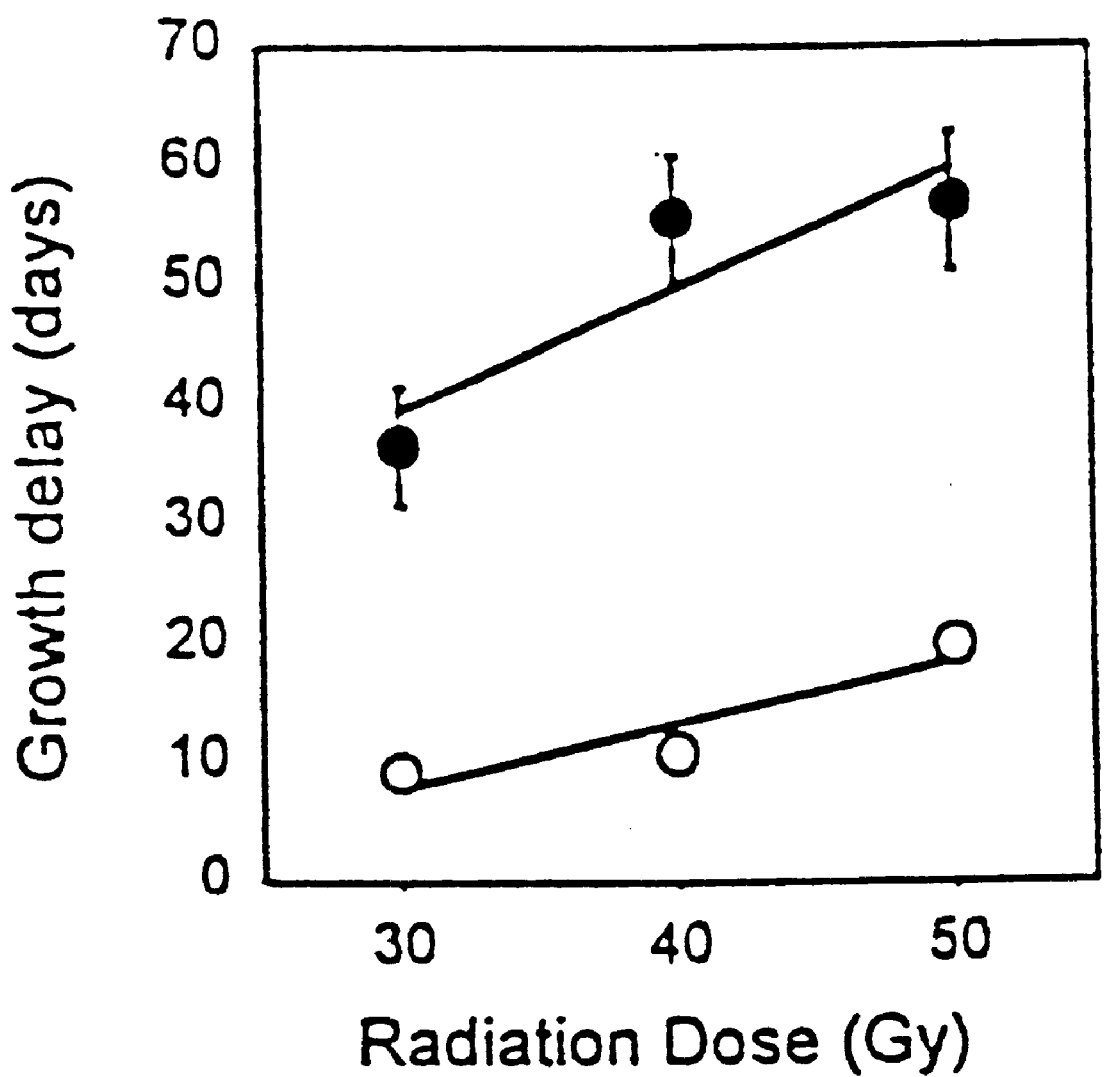
FIG. 3 shows the effect of a COX-2 inhibitor on dose-dependent and radiation-induced delay in tumor growth.

The entire procedure for treatment with a COX-2 inhibitor and local tumor irradiation was the same as that described in FIGS. 2–3. Here, the single doses of γ-radiation ranged from 25 to 80 Gy. Mice were checked for the presence of tumor at the irradiated site at 2- to 7-day intervals for up to 120 days, at which time $TCD_{50}$ values were calculated. $TCD_{50}$ values (tumor control dose 50 designates a radiation dose yielding 50% control [regression] of local tumor) were computed by use of the logistic model (Finney, Quartel response and the tolerance distribution. Statistical methods in biological Assay, $2^{nd}$ Ed., 1952) and shown in FIG. 4 (•-radiation only and ▲-COX-2 inhibitor plus radiation. Horizontal bars represent 95% confidence intervals, at the $TCD_{50}$ dose level. Five of 60 mice that received a COX-2 inhibitor plus radiation died of unknown causes. The dead mice were excluded from $TCD_5$ analysis. $TCD_{50}$ assays contained 57 mice that received radiation only and 55 mice that received a combination of the COX-2 inhibitor and radiation.

Figure 4:
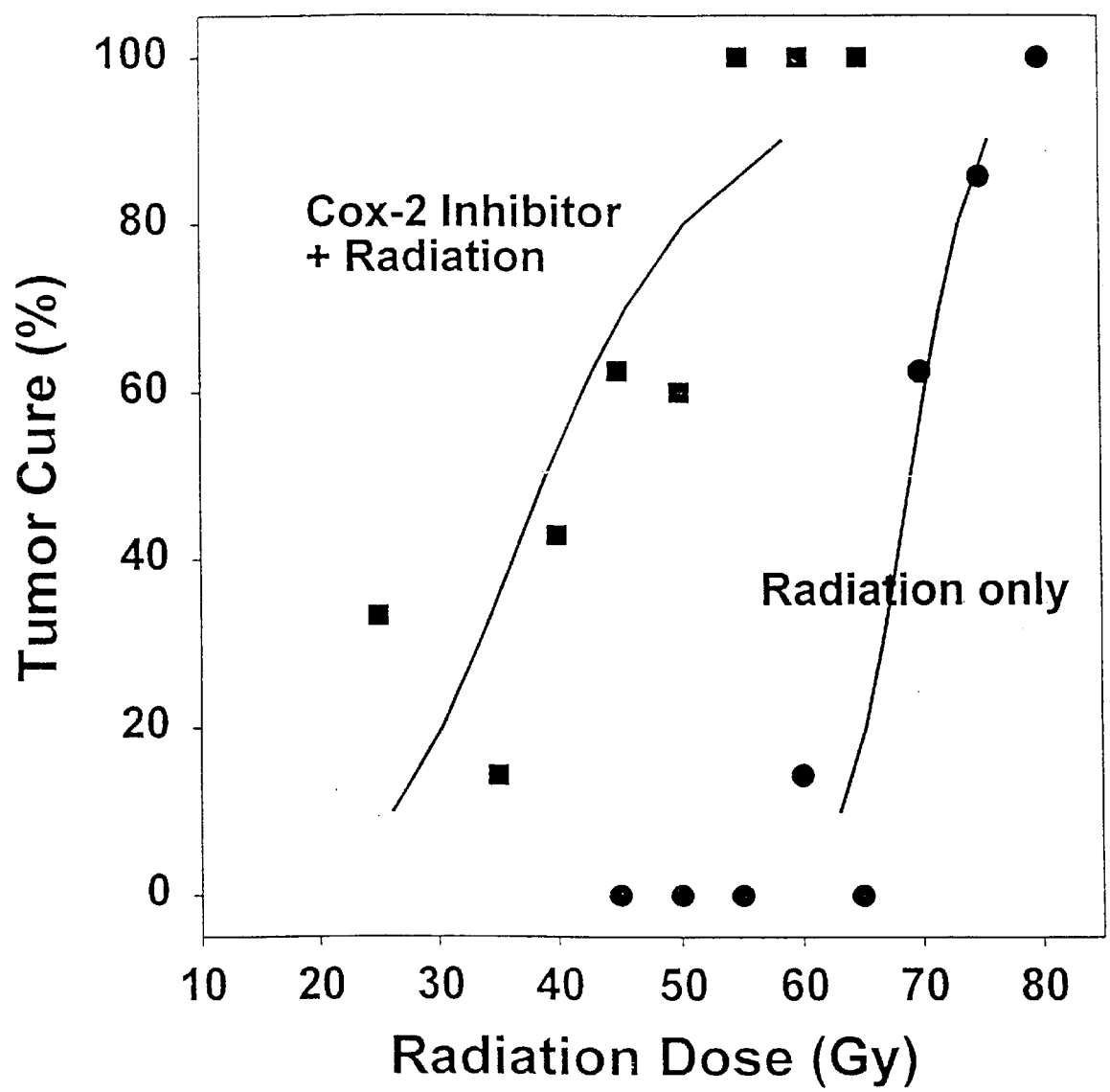
FIG. 4 shows the effect of a COX-2 inhibitor on tumor cure by radiation.

A COX-2 inhibitor co-treatment increased the effect of tumor irradiation, as shown by both tumor growth delay (FIGS. 2 and 3) and tumor cure rate (FIG. 4). The growth delay after the combined treatment was more than the sum of growth delays caused by either irradiation alone or a COX-2 inhibitor alone (FIG. 2). Tumors in control mice required 4.6 days (95% CI=3.9–5.4 days) to grow from 8 to 12 mm in diameter. Mice treated with a COX-2 inhibitor required 7.1 days (95% CI=5.0–9.2 days) (P=0.003), mice treated with 30 Gy required 13.6 days (95% CI=10.5–16.7 days), and mice treated with both agents required 43.5 days (95% CI=30.8–56.2 days) (P=0.001 compared with radiation-only group). The efficacy of irradiation was enhanced by a factor of 3.64 (95% CI=3.42–3.86), determined from the curves in FIG. 3, which plot the magnitude of tumor growth delay as a function of radiation dose with or without treatment with a COX-2 inhibitor. This compound also greatly enhanced the tumor cure rate after irradiation (FIG. 4). The $TCD_{50}$ value was reduced from 69.2 Gy (95% CI=65.7–72.7 GY) in the irradiation-only group to 39.2 Gy (95% CI=31.1–44.6 Gy) in the combination-treatment group. The enhancement factor was 1.77 (95% CI=1.5 1–1.99). obtained by dividing the $TCD_{50}$ value of the radiation-alone group by the combination-treatment group. The 95% CI's were obtained by use of Fieller's theorem (Heron, J. Statist. Comput. Simul., 1975, 3, 265–74).

A COX-2 inhibitor dramatically enhanced the tumor response to radiation, as evidenced by the increase in tumor growth delay and the augmentation of tumor curability. The enhancement factors were 3.64 and 1.77, respectively, greater than the enhancement factors of 1.4 and 1.26 for radiation-indomethacin and radiation alone, respectively.

All documents referenced herein are incorporated by reference.

Although this invention has been described with respect to specific embodiments, the details of these embodiments are not to be construed as limitations.

What is claimed is:

1. A method for treating a neoplasia in a subject in need of such treatment wherein the method comprises treating the subject with an amount of radiation and a radiation-potentiating amount of a COX-2 inhibiting compound selected from the group consisting of celecoxib and 4-[5-(4-chlorophenyl)-3-trifluoromethyl-1H-pyrazol-1-yl] benzenesulfonamide wherein:

the amount of radiation and the amount of the COX-2 inhibiting compound together comprise a neoplasia-treating-effective amount of the COX-2 inhibiting compound and the radiation; and the neoplasia is sensitive to such treatment.

2. The method of claim 1 wherein the neoplasia is selected from the group consisting of lung cancer; breast cancer; gastrointestinal cancer; bladder cancer; head and neck cancer; cervical cancer; colorectal cancer; prostate cancer; and pancreatic cancer.

3. The method of claim 2 wherein the neoplasia is lung cancer.

4. The method of claim 2 wherein the neoplasia is breast cancer.

5. The method of claim 2 wherein the neoplasia is gastrointestinal cancer.

6. The method of claim 2 wherein the neoplasia is bladder cancer.

7. The method of claim 2 wherein the neoplasia is head and neck cancer.

8. The method of claim 2 wherein the neoplasia is cervical cancer.

9. The method of claim 2 wherein the neoplasia is colorectal cancer.

10. The method of claim 2 wherein the neoplasia is prostate cancer.

11. The method of claim 2 wherein the neoplasia is pancreatic cancer.

12. The method of claim 11 wherein the amount of the COX-2 inhibiting compound with which the subject is treated is in the range of about 0.1 to about 10,000 mg per day.

13. The method of claim 12 wherein the amount of the COX-2 inhibiting compound with which the subject is treated is in the range of about 1.0 to about 1,000 mg per day.

14. The method of claim 1 wherein the amount of the COX-2 inhibiting compound with which the subject is treated is at least about 6 mg/kg of body weight per day.

15. The method of claim 1 wherein the COX-2 inhibiting compound is celecoxib.

16. The method of claim 1 wherein the COX-2 inhibiting compound is 4-[5-(4-chlorophenyl)-3-trifluoromethyl-1H-pyrazol-1-yl]benzenesulfonamide.

17. A method for treating a neoplasia in a subject in need of such treatment wherein the method comprises treating the subject with an amount of radiation and a radiation-potentiating amount of a COX-2 inhibiting compound selected from the group consisting of celecoxib and 4-[5-(4-chlorophenyl)-3-trifluoromethyl-1H-pyrazol-1-yl] benzenesulfonamide wherein:

the amount of radiation and the amount of the COX-2 inhibiting compound together comprise a neoplasia-treating-effective amount of the COX-2 inhibiting compound and the radiation;

the amount of the COX-2 inhibiting compound is at least about 6 mg/kg of body weight per day; and the neoplasia is sensitive to such treatment.

18. The method of claim 17 wherein the COX-2 inhibiting compound is celecoxib.

19. The method of claim 17 wherein the COX-2 inhibiting compound is 4-[5-(4-chlorophenyl)-3-trifluoromethyl-1H-pyrazol-1-yl]benzenesulfonamide.

20. A method for treating a neoplasia in a subject in need of such treatment wherein the method comprises treating the subject with an amount of radiation and a radiation-potentiating amount of a COX-2 inhibiting compound selected from the group consisting of celecoxib and 4-[5-(4-chlorophenyl)-3-trifluoromethyl-1H-pyrazol-1-yl] benzenesulfonamide wherein:

the amount of radiation and the amount of the COX-2 inhibiting compound together comprise a neoplasia-treating-effective amount of the COX-2 inhibiting compound and the radiation;

the amount of the COX-2 inhibiting compound is in the range of about 0.1 mg to about 10,000 mg per day; and the neoplasia is sensitive to such treatment.

21. The method of claim 21 wherein the amount of the COX-2 inhibiting compound is in the range of about 1 mg to about 1,000 mg per day.

22. The method of claim 22 wherein the COX-2 inhibiting compound is celecoxib.

23. The method of claim 22 wherein the COX-2 inhibiting compound is 4-[5-(4-chlorophenyl)-3-trifluoromethyl-1H-pyrazol-1-yl]benzenesulfonamide.

* * * * *